(12) United States Patent
Vetter et al.

(10) Patent No.: US 12,152,029 B2
(45) Date of Patent: Nov. 26, 2024

(54) CRYSTALLINE FORMS OF A MAGL INHIBITOR

(71) Applicant: H. Lundbeck A/S, Valby (DK)

(72) Inventors: Thomas Vetter, Valby (DK); Martin Juhl, Valby (DK); Heidi Lopez De Diego, Valby (DK); Cheryl A. Grice, Redwood City, CA (US); John J. M. Wiener, San Diego, CA (US); Daniel J. Buzard, San Diego, CA (US); Amy Allan, San Diego, CA (US); Susana Del Rio Gancedo, Edinburgh (GB); Samuel George Andrew, Edinburgh (GB); Antonio Cincotti, Edinburgh (GB); Adam Ross Patterson, Edinburgh (GB); Richard James Edwards, Edinburgh (GB)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 18/051,654

(22) Filed: Nov. 1, 2022

(65) Prior Publication Data

US 2023/0265095 A1   Aug. 24, 2023

Related U.S. Application Data

(60) Provisional application No. 63/274,887, filed on Nov. 2, 2021.

(51) Int. Cl.
*C07D 471/10* (2006.01)

(52) U.S. Cl.
CPC ........ *C07D 471/10* (2013.01); *C07B 2200/13* (2013.01)

(58) Field of Classification Search
CPC .......................... C07D 471/10; C07B 2200/13
See application file for complete search history.

(56) References Cited

U.S. PATENT DOCUMENTS 10,266,497 B2 * 4/2019 Grice ...................... A61P 37/02

FOREIGN PATENT DOCUMENTS

| WO | WO-2018217805 A1 * | 11/2018 | ......... A61K 31/4155 |
| WO | WO-2020112905 A1 * | 6/2020 | ........... A61K 31/407 |

OTHER PUBLICATIONS

Blankman et al. A comprehensive profile of brain enzymes that hydrolyze the endocannabinoid 2-arachidonoylglycerol. Chem. Biol. 14:1347-1356 (2007).
Gil-Ordonez et al. Monoacylglycerol lipase (MAGL) as a promising therapeutic target. Biochem Pharmacol 157:18-32 (2018).
Grabner et al. Monoglyceride lipase as a drug target: At the crossroads of arachidonic acid metabolism and endocannabinoid signaling. Pharmacol Ther 175:35-46 (2017).
Katona et al. Endocannabinoid signalling as a synaptic circuit breaker in neurological disease. Nat Med. 14(9):923-93 (2008).
Mulvihill et al. Therapeutic potential of monoacylglycerol lipase inhibitors. Life Sci 92(8-9):492-497 (2013).
Nomura et al. Endocannabinoid hydrolysis generates brain prostaglandins that promote neuroinflammation. Science 334(6057):809-813 (2011).
Turcotte et al. The CB2 receptor and its role as a regulator of inflammation. Cell. Mol. Life Sci. 73:4449-4470 (2016).
Caira. Crystalline Polymorphism of Organic Compounds. Topics in Current Chemistry. 198:163-208 (Jan. 1998).
PCT/EP2022/080434 International Search Report and Written Opinion dated Feb. 1, 2023.

* cited by examiner

*Primary Examiner* — Bahar Craigo
*Assistant Examiner* — Manahil Mirghani Ali Abdalhameed
(74) *Attorney, Agent, or Firm* — WILSON SONSINI GOODRICH & ROSATI

(57) ABSTRACT

Described herein are new crystalline forms of the MAGL inhibitor 1-(1-(2-(pyrrolidin-1-yl)-4-(trifluoromethyl)benzyl)-1,8-diazaspiro[4.5]decane-8-carbonyl)-1H-pyrazole-3-carboxylic acid, or a pharmaceutically acceptable salt thereof.

25 Claims, 21 Drawing Sheets

CRYSTALLINE FORMS OF A MAGL INHIBITOR

CROSS-REFERENCE

This application claims the benefit of U.S. Provisional Application No. 63/274,887 filed Nov. 2, 2021.

FIELD OF THE INVENTION

The present invention relates to solid forms of 1-(1-(2-(pyrrolidin-1-yl)-4-(trifluoromethyl)benzyl)-1,8-diazaspiro[4.5]decane-8-carbonyl)-1H-pyrazole-3-carboxylic acid, pharmaceutical compositions comprising such solid forms and methods and uses for treating various disorders that would benefit from inhibition of monoacylglycerol lipase (MAGL).

BACKGROUND OF THE INVENTION

MAGL is a member of the serine hydrolase superfamily. MAGL is expressed throughout the brain, in neurons, microglia, astrocytes, and oligodendrocytes. MAGL is the primary enzyme controlling the degradation of 2-arachidonoylglycerol (2-AG) to arachidonic acid (AA) (Blankman et al. Chem Biol. 2007; Nomura et al. Science. 2011).

2-AG is the most abundant endocannabinoid ligand in the brain where it acts as a retrograde messenger to reduce excessive neurotransmission via the activation of pre-synaptic $CB_1$ receptors (Katona et al., Nat Med. 2008 September; 14(9):923-30), regulating immune response via the activation of microglial $CB_2$ receptors (Turcotte et al. Cell Mol Life Sci. 2016 December; 73(23):4449-4470), and promote neuroprotection via e.g., its effects on oligodendrocyte production and survival (Front Neurosci. 2018 Oct. 26; 12:733).

AA is one of the most abundant fatty acids in the brain and the main precursor of eicosanoids such as prostanoids and leukotrienes that are known inflammatory mediators.

MAGL is at the crossroads between the endocannabinoid and eicosanoid signaling systems. Inhibiting the action or activation of MAGL is a promising therapeutic approach for the prevention or treatment of brain disorders whose pathological hallmarks include excessive neurotransmission, neuroinflammation or neurodegeneration such as Alzheimer's disease (AD), Parkinson's disease (PD), Huntington's disease (HD), multiple sclerosis (MS), amyotrophic lateral sclerosis (ALS), traumatic brain injury, stroke, epilepsy, pain, migraine, addiction, anxiety, depression and other stress-related disorders (Grabner et al. Pharmacol Ther. 2017 July; 175:3546; Mulvihill et al. Life Sci. 2013 Mar. 19; 92(8-9):492-7; Gil-Ordóñez et al. Biochem Pharmacol. 2018 November; 157:18-32).

WO 2018/217805 discloses 1-(1-(2-(pyrrolidin-1-yl)-4-(trifluoromethyl)benzyl)-1,8-diazaspiro[4.5]decane-8-carbonyl)-1H-pyrazole-3-carboxylic acid as an example of a compound which is a MAGL inhibitor promising for treating disorders, wherein MAGL inhibition may be beneficial.

The development of a pharmaceutical compound is highly complex, because it is not possible to predict from previous experience if various solid forms of a compound exist, let alone how to make them.

Even after a solid form has been manufactured, the identification and selection of a solid form for further pharmaceutical development are complex, given that a change in a solid form may affect a variety of physical and chemical abilities which are unpredictable and may provide benefits or drawbacks in areas of pharmaceutical development such as processing, formulation, stability, bioavailability, or storage.

From this background it is still not possible to predict whether a particular compound or salt of a compound will form polymorphs, whether any such polymorphs will be suitable for commercial use in a therapeutic composition or which polymorphs will display such desirable properties. Hence, there is still an unmet process for making solid forms with desirable properties for further pharmaceutical development.

SUMMARY OF THE INVENTION

An object of the invention is to provide a solid form of 1-(1-(2-(pyrrolidin-1-yl)-4-(trifluoromethyl)benzyl)-1,8-diazaspiro[4.5]decane-8-carbonyl)-1H-pyrazole-3-carboxylic acid (Compound (I)) suitable for pharmaceutical development.

Accordingly, in a first aspect of the invention is provided a crystalline form of Compound (I), or a pharmaceutically acceptable salt thereof.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 having at least one of the following properties:
  a) an X-ray powder diffraction (XRPD) obtained using $CuK_{\alpha 1}$ radiation ($\lambda=1.5406$ Å) showing an XRPD pattern substantially the same as shown in FIG. 1;
  b) an X-ray powder diffraction (XRPD) pattern obtained using $CuK_{\alpha 1}$ radiation ($\lambda=1.5406$ Å) showing characteristic peaks at the following 2θ-angles: 8.60, 10.72, 11.12, 14.17, 15.30, 19.08, 22.70, and 24.30°;
  c) a thermo-gravimetric analysis (TGA) substantially similar to the one set forth in FIG. 2;
  d) combination thereof.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 having a crystal form characterized by an XRPD obtained using $CuK_{\alpha 1}$ radiation ($\lambda=1.5406$ Å) showing peaks at the following 2θ-angles: 8.60, 10.72, 11.12, 14.17, 15.30, 19.08, 22.70, and 24.300.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid form 7 having at least one of the following properties:
  a) an X-ray powder diffraction (XRPD) obtained using $CuK_{\alpha 1}$ radiation ($\lambda=1.5406$ Å) showing an XRPD pattern substantially the same as shown in FIG. 3;
  b) an X-ray powder diffraction (XRPD) pattern obtained using $CuK_{\alpha 1}$ radiation ($\lambda=1.5406$ Å) showing characteristic peaks at the following 2θ-angles: 8.91, 9.20, 12.17, 14.11, 16.33, 18.46, and 19.90°;
  c) a thermo-gravimetric analysis (TGA) substantially similar to the one set forth in FIG. 4;
  d) combination thereof.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid form 7 having a crystal form characterized by an XRPD obtained using $CuK_{\alpha}$ radiation ($\lambda_1=1.5406$ Å, $\lambda_2=1.5444$ Å) showing peaks at the following 2θ-angles: 8.91, 9.20, 12.17, 14.11, 16.33, 18.46, and 19.900.

In an embodiment, the crystalline form is 1-(1-(2-(pyrrolidin-1-yl)-4-(trifluoromethyl)benzyl)-1,8-diazaspiro[4.5]

decane-8-carbonyl)-1H-pyrazole-3-carboxylic acid acetone solvate having at least one of the following properties:
  a) an X-ray powder diffraction (XRPD) obtained using CuK$_\alpha$ radiation ($\lambda_1$=1.5406 Å, $\lambda_2$=1.5444 Å) showing an XRPD pattern substantially the same as shown in FIG. 5;
  b) an X-ray powder diffraction (XRPD) pattern obtained using CuK$_\alpha$ radiation ($\lambda_1$=1.5406 Å, $\lambda_2$=1.5444 Å) showing characteristic peaks at the following 2θ-angles: 10.19, 11.09, 15.00, 17.86, 19.57, 20.84, 23.74, and 31.34°;
  c) a thermo-gravimetric analysis (TGA) substantially similar to the one set forth in FIG. 6;
  d) combination thereof.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate having a crystal form characterized by an XRPD obtained using CuK$_\alpha$ radiation ($\lambda_1$=1.5406 Å, $\lambda_2$=1.5444 Å) showing peaks at the following 2θ-angles: 10.19, 11.09, 15.00, 17.86, 19.57, 20.84, 23.74, and 31.34°.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1 having at least one of the following properties:
  a) an X-ray powder diffraction (XRPD) obtained using CuK$_\alpha$ radiation ($\lambda_1$=1.5406 Å, $\lambda_2$=1.5444 Å) showing an XRPD pattern substantially the same as shown in FIG. 7;
  b) an X-ray powder diffraction (XRPD) pattern obtained using CuK$_\alpha$ radiation ($\lambda_1$=1.5406 Å, $\lambda_2$=1.5444 Å) showing characteristic peaks at the following 2θ-angles: 7.46, 14.64, 15.09, 16.15, 18.72, 19.34, 25.22, and 25.92°;

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1 having a crystal form characterized by an XRPD obtained using CuK$_\alpha$ radiation ($\lambda_1$=1.5406 Å, $\lambda_2$=1.5444 Å) showing peaks at the following 2θ-angles: 7.46, 14.64, 15.09, 16.15, 18.72, 19.34, 25.22, and 25.92°.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2 having at least one of the following properties:
  a) an X-ray powder diffraction (XRPD) obtained using CuK$_\alpha$ radiation ($\lambda_1$=1.5406 Å, $\lambda_2$=1.5444 Å) showing an XRPD pattern substantially the same as shown in FIG. 8;
  b) an X-ray powder diffraction (XRPD) pattern obtained using CuK$_\alpha$ radiation ($\lambda_1$=1.5406 Å, $\lambda_2$=1.5444 Å) showing characteristic peaks at the following 2θ-angles: 6.67, 11.01, 15.23, 16.06, 16.81, 19.39, 19.77, and 22.84°;

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2 having a crystal form characterized by an XRPD obtained using CuK$_\alpha$ radiation ($\lambda_1$=1.5406 Å, $\lambda_2$=1.5444 Å) showing peaks at the following 2θ-angles: 6.67, 11.01, 15.23, 16.06, 16.81, 19.39, 19.77, 22.84°.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 2 having at least one of the following properties:
  a) an X-ray powder diffraction (XRPD) obtained using CuK$_{\alpha 1}$ radiation ($\lambda$=1.5406 Å) showing an XRPD pattern substantially the same as shown in FIG. 10;
  b) an X-ray powder diffraction (XRPD) pattern obtained using CuK$_{\alpha 1}$ radiation ($\lambda$=1.5406 Å) showing characteristic peaks at the following 2θ-angles: 4.30, 10.16, 12.85, 15.67, 21.54, 23.08°;
  c) a thermo-gravimetric analysis (TGA) substantially similar to the one set forth in FIG. 11; or
  d) combination thereof.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 2 having a crystal form characterized by an XRPD obtained using CuK$_{\alpha 1}$ radiation ($\lambda$=1.5406 Å) showing peaks at the following 2θ-angles: 4.30, 10.16, 12.85, 15.67, 21.54, and 23.080.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 4 having at least one of the following properties:
  a) an X-ray powder diffraction (XRPD) obtained using CuK$_\alpha$ radiation ($\lambda_1$=1.5406 Å, $\lambda_2$=1.5444 Å) showing an XRPD pattern substantially the same as shown in FIG. 14;
  b) an X-ray powder diffraction (XRPD) pattern obtained using CuK$_\alpha$ radiation ($\lambda_1$=1.5406 Å, $\lambda_2$=1.5444 Å) showing characteristic peaks at the following 2θ-angles: 9.05, 11.07, 11.75, 15.31, 18.39, 25.60, 29.67, and 36.40°;
  c) a thermo-gravimetric analysis (TGA) substantially similar to the one set forth in FIG. 15; or
  d) combination thereof.

In an embodiment, the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 4 having a crystal form characterized by an XRPD obtained using CuK$_\alpha$ radiation ($\lambda_1$=1.5406 Å, $\lambda_2$=1.5444 Å) showing peaks at the following 2θ-angles: 9.05, 11.07, 11.75, 15.31, 18.39, 25.60, 29.67, and 36.40°.

In a further aspect is provided a pharmaceutical composition comprising a crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid, or a pharmaceutically acceptable salt, and one or more pharmaceutically acceptable carriers.

In a further aspect is provided a crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid, or a pharmaceutically acceptable salt thereof, for use in the treatment of a disease or disorder that could benefit from inhibition of MAGL.

In an embodiment, the disease or disorder selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

In a further aspect is provided a method of manufacturing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1.

In an embodiment, the process of manufacturing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 comprises the steps of.
  i) providing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate; and
  ii) heating 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate to above 150-180° C. at a minimum of 2 minutes.

In an embodiment, step i) comprises the steps of.
  1a) providing 1-(1-(2-(pyrrolidin-1-yl)-4-(trifluoromethyl)benzyl)-1,8-diazaspiro[4.5]decane-8-carbonyl)-1H-pyrazole-3-carboxylic acid;
  1b) adding acetone to provide a solution comprising 1-(1-(2-(pyrrolidin-1-yl)-4-(trifluoromethyl)benzyl)-1,8-diazaspiro[4.5]decane-8-carbonyl)-1H-pyrazole-3-carboxylic; and
  1c) maturing the solution comprising 1-(1-(2-(pyrrolidin-1-yl)-4-(trifluoromethyl)benzyl)-1,8-diazaspiro[4.5]decane-8-carbonyl)-1H-pyrazole-3-carboxylic acid.

In an embodiment, the acetone in step 1b) is added between 5-50° C.

In an embodiment, the mixture comprising 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate is matured in step 1c) for at least 24 hours, preferably for at least 72 hours.

In a separate embodiment, the process of manufacturing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 comprises the step of:
  i) providing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1; and
  ii) drying crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1 to provide crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1.

The crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 have shown to be thermodynamically stable In an embodiment, step i) comprises the steps of
  1a) providing 1-(1-(2-(pyrrolidin-1-yl)-4-(trifluoromethyl)benzyl)-1,8-diazaspiro[4.5]decane-8-carbonyl)-1H-pyrazole-3-carboxylic acid, and
  1b) adding 1,4-dioxane at room temperature to provide a mixture comprising 1-(1-(2-(pyrrolidin-1-yl)-4-(trifluoromethyl)benzyl)-1,8-diazaspiro[4.5]decane-8-carbonyl)-1H-pyrazole-3-carboxylic acid and stirring the solution at least 24 hours at 0-10° C., preferably at 5° C.

In an embodiment, the solution is stirred in step 1b) for at least 36 hours, preferably for 48 hours.

In another embodiment, the process of manufacturing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 comprising the step of:
  i) providing 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2; and
  ii) drying 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2 to provide crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1.

In an embodiment, step i) comprises the step of:
  1a) providing 1-(1-(2-(pyrrolidin-1-yl)-4-(trifluoromethyl)benzyl)-1,8-diazaspiro[4.5]decane-8-carbonyl)-1H-pyrazole-3-carboxylic acid, and
  1b) adding 1,4-dioxane at room temperature to provide a mixture comprising 1-(1-(2-(pyrrolidin-1-yl)-4-(trifluoromethyl)benzyl)-1,8-diazaspiro[4.5]decane-8-carbonyl)-1H-pyrazole-3-carboxylic acid followed by stirring the solution at least 24 hours at 40-60° C., preferably at 50° C.

In an embodiment, the mixture is stirred in step 1b) for at least 36 hours, preferably 48 hours.

In an embodiment, the drying in step ii) is performed in vacuum at room temperature.

INCORPORATION BY REFERENCE

All publications and patent applications mentioned in this specification are herein incorporated by reference to the extent applicable and relevant.

DETAILED DESCRIPTION OF THE INVENTION

Definitions

Figure 1:
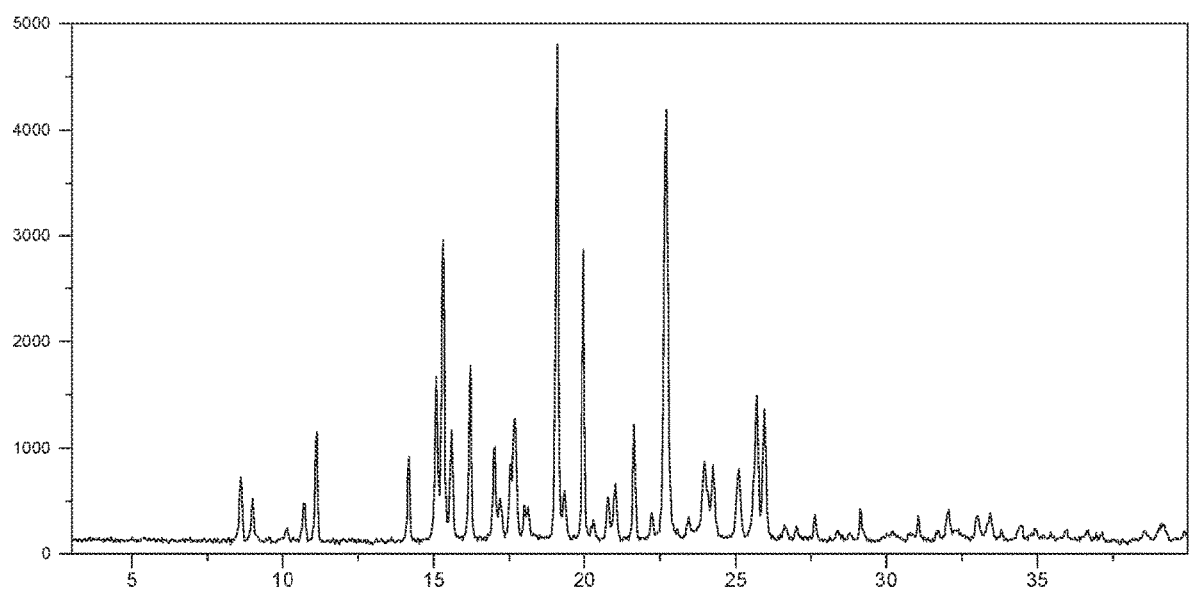
FIG. 1 illustrates an X-ray powder diffraction (XRPD) pattern of Compound (I) form 1. X-axis: diffraction angle (°2θ); Y-axis: intensity (counts).

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound (I), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "inhibits", "inhibiting", or "inhibitor" of an enzyme as used herein, refer to inhibition of enzymatic activity.

The term "subject" as used herein, refers to an animal which is the object of treatment, observation or experiment. By way of example only, a subject may be, but is not limited to, a mammal including, but not limited to, a human. In an embodiment, the subject is a human.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

The X-ray diffraction data provided herein is indicated to a precision of ±0.1°2θ.

Compounds

The compound, 2-(2-((4-(((1,1,1,3,3,3-hexafluoropropan-2-yl)oxy)carbonyl)piperazin-1-yl)methyl)-5-(trifluoromethyl)phenoxy)-2-methylpropanoic acid, designated herein as Compound (I), has the structure:

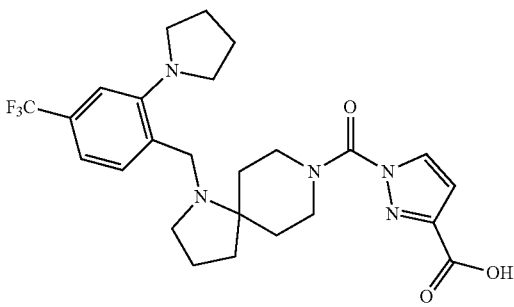 [SMILES: O=C(O)c1ccn(C(=O)N2CCC3(CCCN3Cc3ccc(C(F)(F)F)cc3N3CCCC3)CC2)n1]

WO 2018/217805 discloses amorphous 2-(2-((4-(((1,1,1,3,3,3-hexafluoropropan-2-yl)oxy)carbonyl)piperazin-1-yl)methyl)-5-(trifluoromethyl)phenoxy)-2-methylpropanoic acid, designated herein as Amorphous Compound (I). The present invention relates to crystalline forms of Compound (I), and the use of the compounds for treating various disease and disorder which is believed to be linked to the regulation of endocannabinoid system signaling activities. The present invention further provides crystalline forms of Compound (I) described herein as "Compound (I) form 1", "Compound (I) form 7", "Compound (I) 1,4-dioxane solvate form 1", "Compound (I) 1,4-dioxane solvate form 2" and "Compound (I) acetone solvate". These are free forms of Compound (I). The term "freeform" refers to Compound (I) in non-salt form. The term "solvate" refers to substance containing Compound (I), but also containing molecules of solvent incorporated into the crystal lattice.

The present invention further provides pharmaceutically acceptable salts of Compound (I).

Further described herein are several mono-hydrochloride salts of Compound (I) designated as "amorphous Compound (I) HCl", "Compound (I) HCl form 1", "Compound (I) HCl form 2", "Compound (I) HCl 2-MeTHF solvate", "Compound (I) HCl form 4", "Compound (I) HCl form 5", and "Compound (I) HCl form 6"

The term "pharmaceutically acceptable salts" in reference to Compound (I) refers to a salt of Compound (I), which does not cause significant irritation to a mammal to which it is administered and does not substantially abrogate the biological activity and properties of the compound.

While not intending to be bound by any particular theory, certain solid forms have different physical and chemical properties, e.g., stability, solubility and dissolution rate, appropriate for pharmaceutical and therapeutic dosage forms. Moreover, while not wishing to be bound by any particular theory, certain solid forms have different physical and chemical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

Embodiments of the Invention

In the following, embodiments of the invention are disclosed. The first embodiment is denoted E1, the second embodiment is denoted E2 and so forth.

E1. A crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid, or a pharmaceutically acceptable salt thereof.

E2. The crystalline form according to embodiment E1, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 having at least one of the following properties:
  a) an X-ray powder diffraction (XRPD) obtained using CuK$_{\alpha 1}$ radiation ($\lambda$=1.5406 Å) showing an XRPD pattern substantially the same as shown in FIG. 1;
  b) an X-ray powder diffraction (XRPD) pattern obtained using CuK$_{\alpha 1}$ radiation ($\lambda$=1.5406 Å) showing characteristic peaks at the following 2θ-angles: 8.60, 10.72, 11.12, 14.17, 15.30, 19.08, 22.70, and 24.30°;
  c) a thermo-gravimetric analysis (TGA) substantially similar to the one set forth in FIG. 2;
  d) combination thereof.

E3. The crystalline form according to embodiment E2, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 having a crystal form characterized by an XRPD obtained using CuK$_{\alpha 1}$ radiation ($\lambda$=1.5406 Å) showing peaks at the following 2θ-angles: 8.60, 10.72, 11.12, 14.17, 15.30, 19.08, 22.70, and 24.30°.

Figure 3:
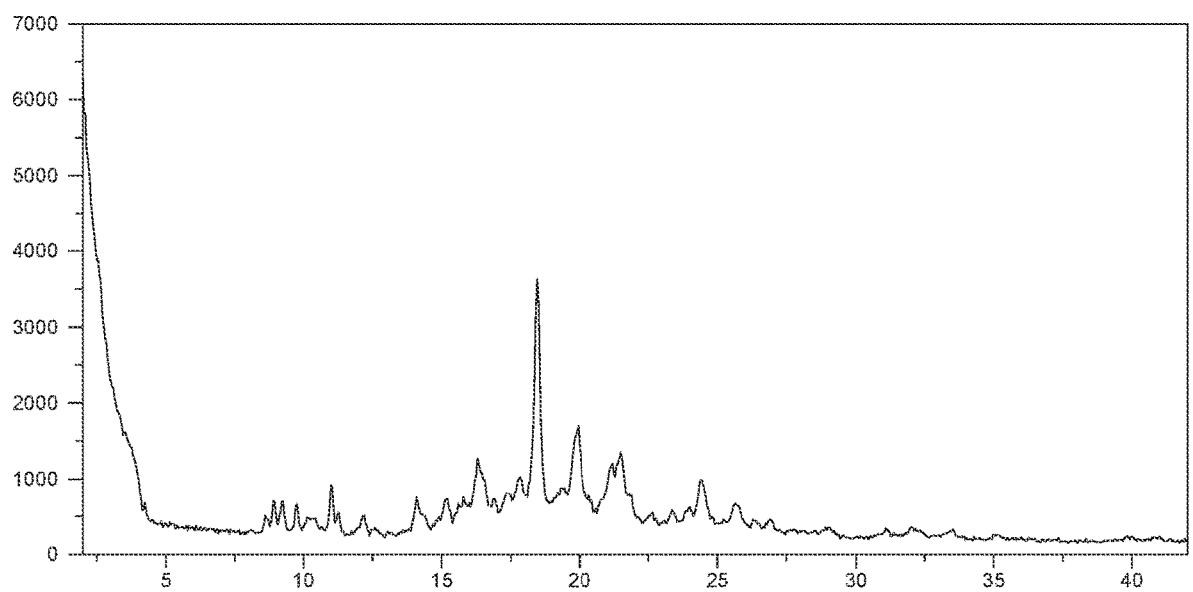
FIG. 3 illustrates an X-ray powder diffraction (XRPD) pattern of Compound (I) form 7. X-axis: diffraction angle (°2θ); Y-axis: intensity (counts).

E4. The crystalline form according to embodiment E1, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid form 7 having at least one of the following properties:
  a) an X-ray powder diffraction (XRPD) obtained using CuK$_{\alpha 1}$ radiation ($\lambda$=1.5406 Å) showing an XRPD pattern substantially the same as shown in FIG. 3;
  b) an X-ray powder diffraction (XRPD) pattern obtained using CuK$_{\alpha 1}$ radiation ($\lambda$=1.5406 Å) showing characteristic peaks at the following 2θ-angles: 8.91, 9.20, 12.17, 14.11, 16.33, 18.46, and 19.90°;
  c) a thermo-gravimetric analysis (TGA) substantially similar to the one set forth in FIG. 4;
  d) combination thereof.

E5. The crystalline form according to embodiment E4, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid form 7 having a crystal form characterized by an XRPD obtained using CuK$_{\alpha}$ radiation ($\lambda_1$=1.5406 Å, $\lambda_2$=1.5444 Å) showing peaks at the following 2θ-angles: 8.91, 9.20, 12.17, 14.11, 16.33, 18.46, and 19.90°.

Figure 5:
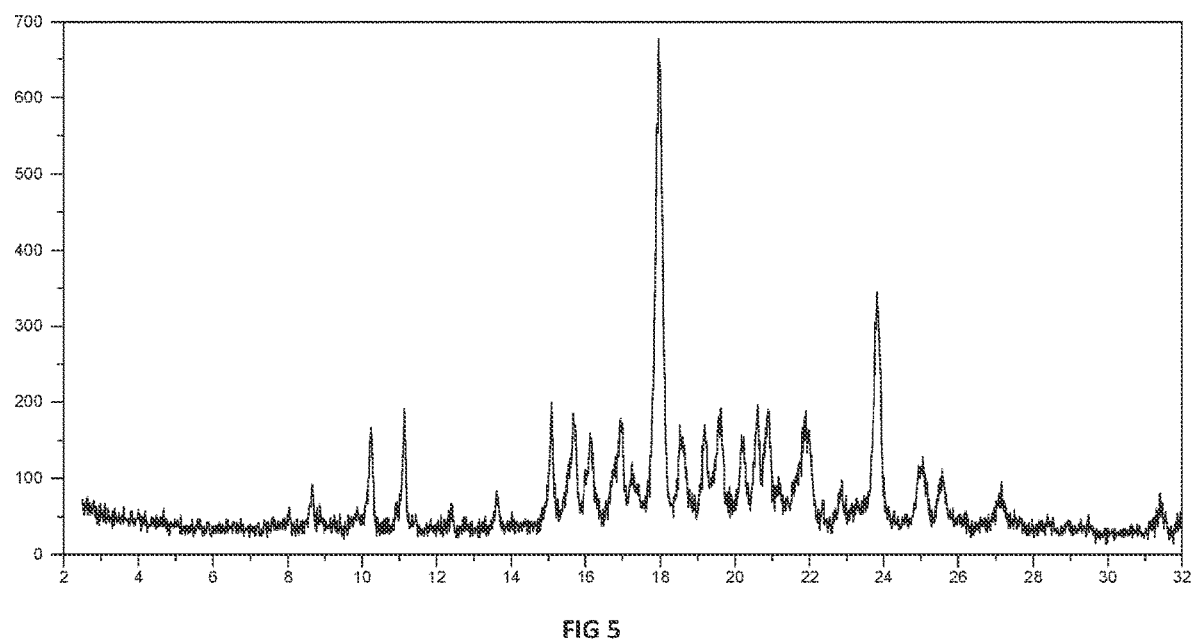
FIG. 5 illustrates an X-ray powder diffraction (XRPD) pattern of Compound (I) acetone solvate. X-axis: diffraction angle (°2θ); Y-axis: intensity (counts).

E6. The crystalline form according to embodiment E1, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate having at least one of the following properties:
  a) an X-ray powder diffraction (XRPD) obtained using CuK$_{\alpha}$ radiation ($\lambda_1$=1.5406 Å, $\lambda_2$=1.5444 Å) showing an XRPD pattern substantially the same as shown in FIG. 5;
  b) an X-ray powder diffraction (XRPD) pattern obtained using CuK$_{\alpha}$ radiation ($\lambda_1$=1.5406 Å, $\lambda_2$=1.5444 Å) showing characteristic peaks at the following 2θ-angles: 10.19, 11.09, 15.00, 17.86, 19.57, 20.84, 23.74, and 31.34°;
  c) a thermo-gravimetric analysis (TGA) substantially similar to the one set forth in FIG. 6;
  d) combination thereof.

E7. The crystalline form according to embodiment E6, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate having a crystal form characterized by an XRPD obtained using CuK$_\alpha$ radiation ($\lambda_1$=1.5406 Å, $\lambda_2$=1.5444 Å) showing peaks at the following 2θ-angles: 10.19, 11.09, 15.00, 17.86, 19.57, 20.84, 23.74, and 31.34°.

Figure 7:
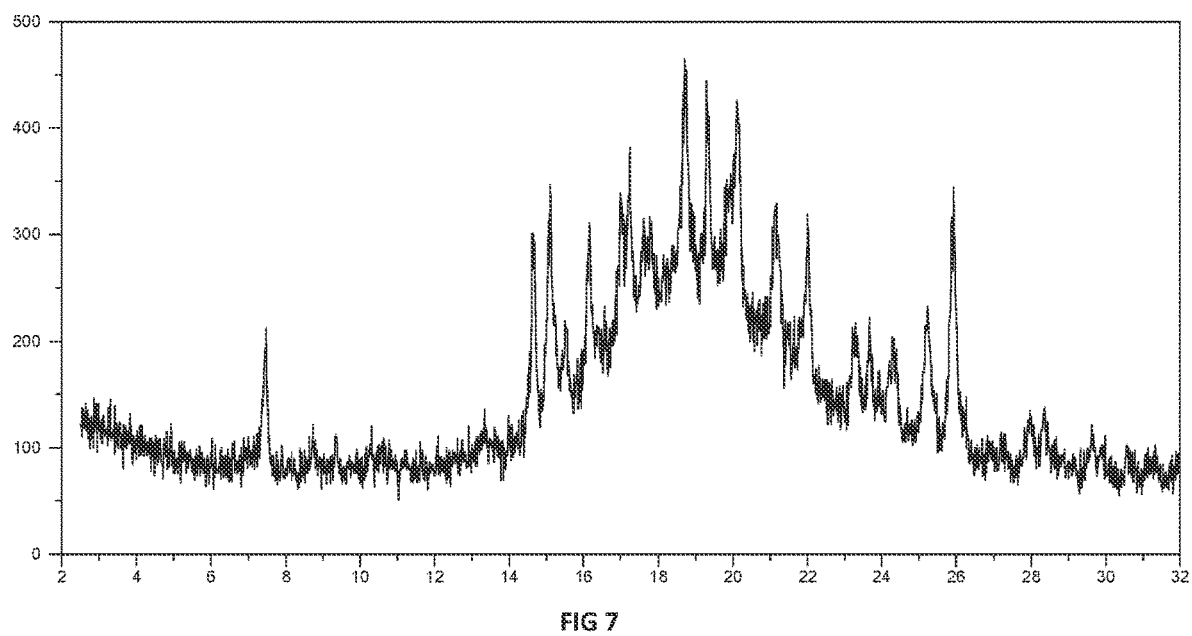
FIG. 7 illustrates an X-ray powder diffraction (XRPD) pattern of Compound (I) 1,4-dioxane solvate form 1. X-axis: diffraction angle (°2θ); Y-axis: intensity (counts).

E8. The crystalline form according to embodiment E1, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1 having at least one of the following properties:
  a) an X-ray powder diffraction (XRPD) obtained using CuK$_\alpha$ radiation ($\lambda_1$=1.5406 Å, $\lambda_2$=1.5444 Å) showing an XRPD pattern substantially the same as shown in FIG. 7;
  b) an X-ray powder diffraction (XRPD) pattern obtained using CuK$_\alpha$ radiation ($\lambda_1$=1.5406 Å, $\lambda_2$=1.5444 Å) showing characteristic peaks at the following 2θ-angles: 7.46, 14.64, 15.09, 16.15, 18.72, 19.34, 25.22, and 25.92°;

E9. The crystalline form according to embodiment E8, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1 having a crystal form characterized by an XRPD obtained using CuK$_\alpha$ radiation ($\lambda_1$=1.5406 Å, $\lambda_2$=1.5444 Å) showing peaks at the following 2θ-angles: 7.46, 14.64, 15.09, 16.15, 18.72, 19.34, 25.22, and 25.92°.

Figure 8:
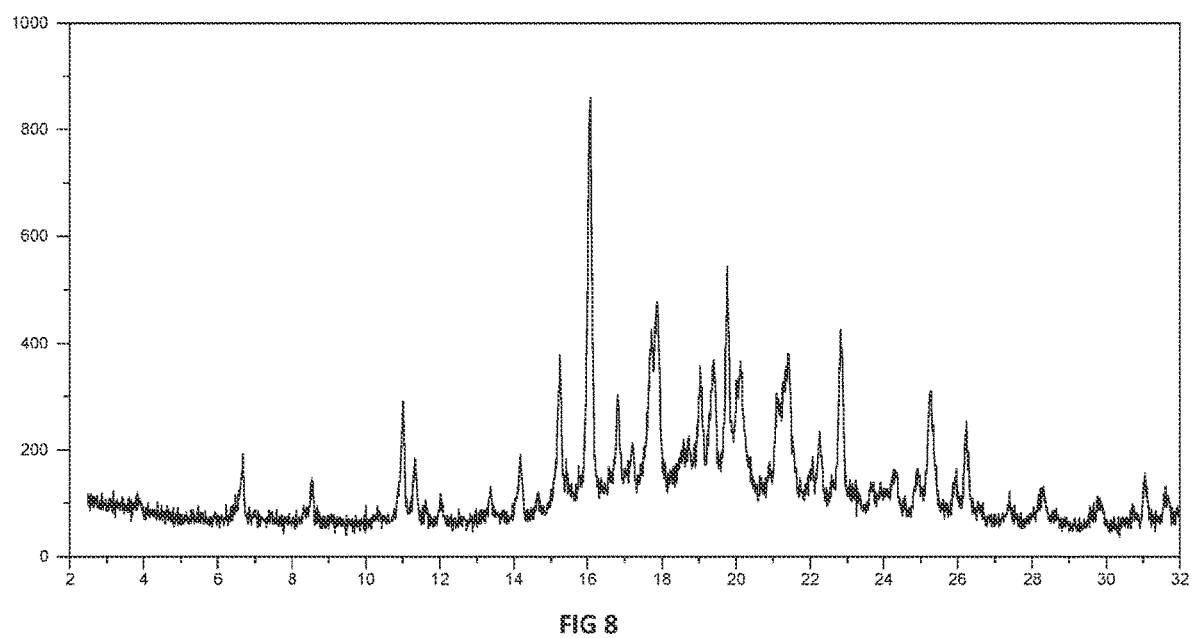
FIG. 8 illustrates an X-ray powder diffraction (XRPD) pattern of Compound (I) 1,4-dioxane solvate form 2. X-axis: diffraction angle (°2θ); Y-axis: intensity (counts).

E10. The crystalline form according to embodiment E1, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2 having at least one of the following properties:
  a) an X-ray powder diffraction (XRPD) obtained using CuK$_\alpha$ radiation ($\lambda_1$=1.5406 Å, $\lambda_2$=1.5444 Å) showing an XRPD pattern substantially the same as shown in FIG. 8;
  b) an X-ray powder diffraction (XRPD) pattern obtained using CuK$_\alpha$ radiation ($\lambda_1$=1.5406 Å, $\lambda_2$=1.5444 Å) showing characteristic peaks at the following 2θ-angles: 6.67, 11.01, 15.23, 16.06, 16.81, 19.39, 19.77, and 22.84°;

E11. The crystalline form according to embodiment E10, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2 having a crystal form characterized by an XRPD obtained using CuK$_\alpha$ radiation ($\lambda_1$=1.5406 Å, $\lambda_2$=1.5444 Å) showing peaks at the following 2θ-angles: 6.67, 11.01, 15.23, 16.06, 16.81, 19.39, 19.77, 22.84°.

Figure 10:
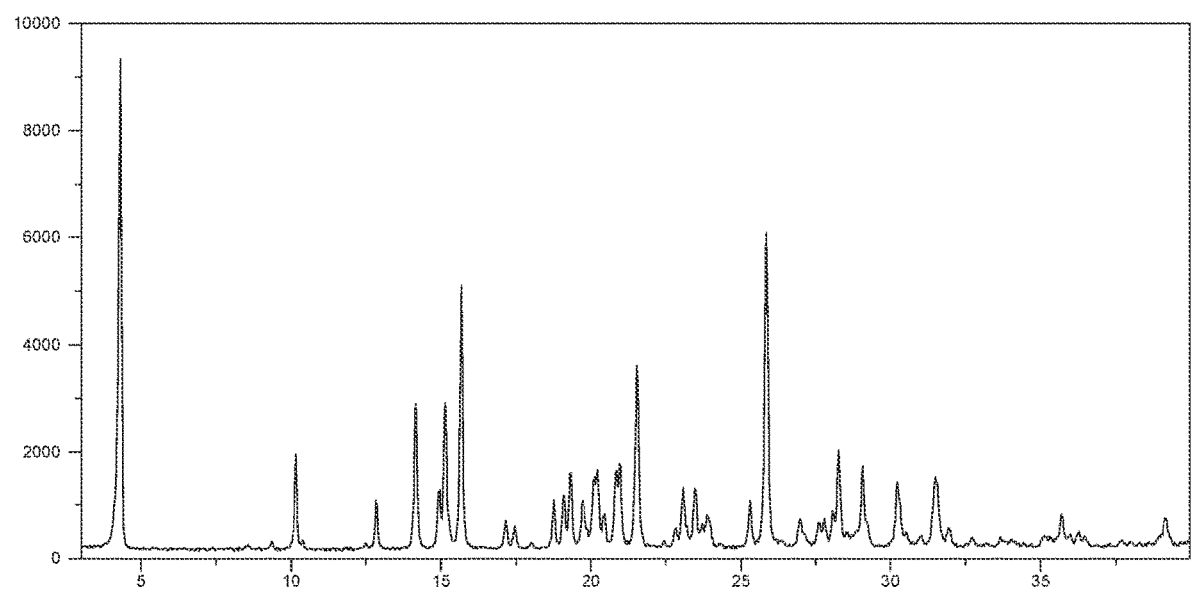
FIG. 10 illustrates an X-ray powder diffraction (XRPD) pattern of Compound (I) HCl salt form 2. X-axis: diffraction angle (°2θ); Y-axis: intensity (counts).
Figure 11:
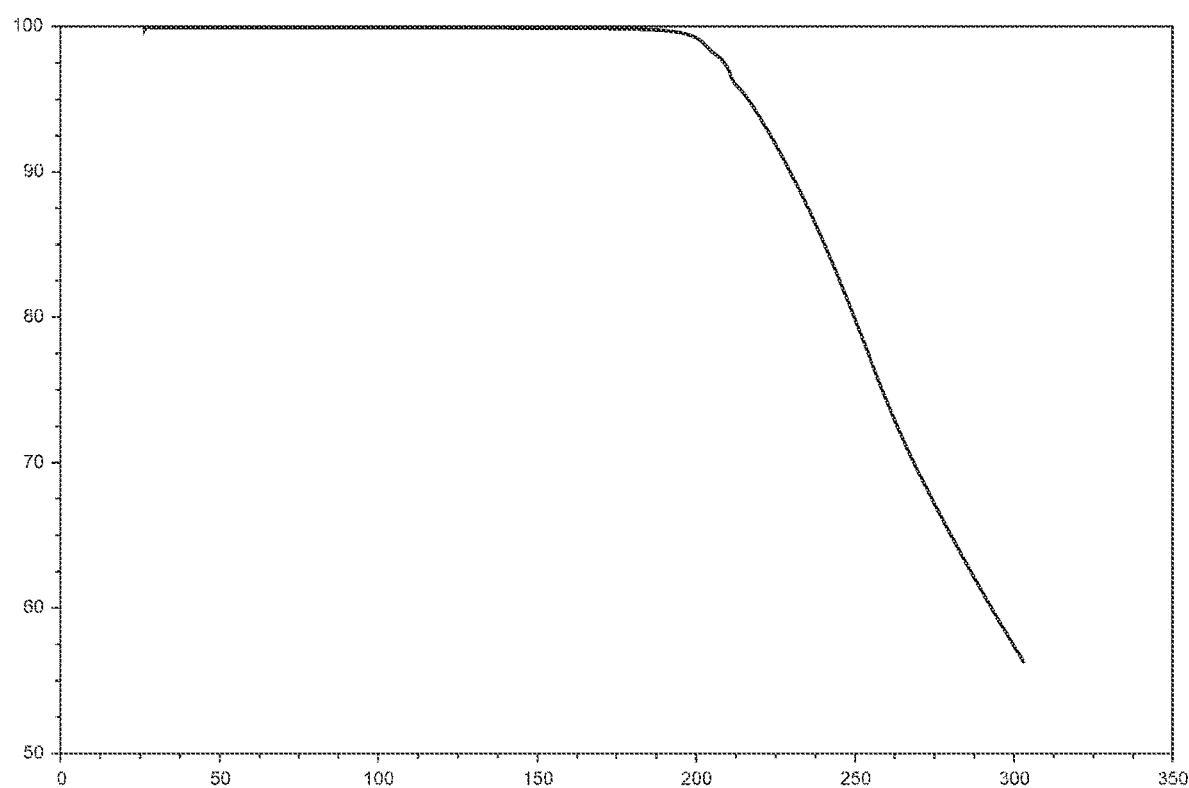
FIG. 11 illustrates a thermo-gravimetric analysis (TGA) thermogram of Compound (I) HCl salt form 2. X-axis: Temperature (° C.); Y-axis: Weight (%).

E12. The crystalline form according to embodiment E1, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 2 having at least one of the following properties:
  a) an X-ray powder diffraction (XRPD) obtained using CuK$_{\alpha 1}$ radiation ($\lambda$=1.5406 Å) showing an XRPD pattern substantially the same as shown in FIG. 10;
  b) an X-ray powder diffraction (XRPD) pattern obtained using CuK$_{\alpha 1}$ radiation ($\lambda$=1.5406 Å) showing characteristic peaks at the following 2θ-angles: 4.30, 10.16, 12.85, 15.67, 21.54, 23.08°;
  c) a thermo-gravimetric analysis (TGA) substantially similar to the one set forth in FIG. 11; or
  d) combination thereof.

E13. The crystalline form according to embodiment E12, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 2 having a crystal form characterized by an XRPD obtained using CuK$_{\alpha 1}$ radiation ($\lambda$=1.5406 Å) showing peaks at the following 2θ-angles: 4.30, 10.16, 12.85, 15.67, 21.54, and 23.08°.

Figure 14:
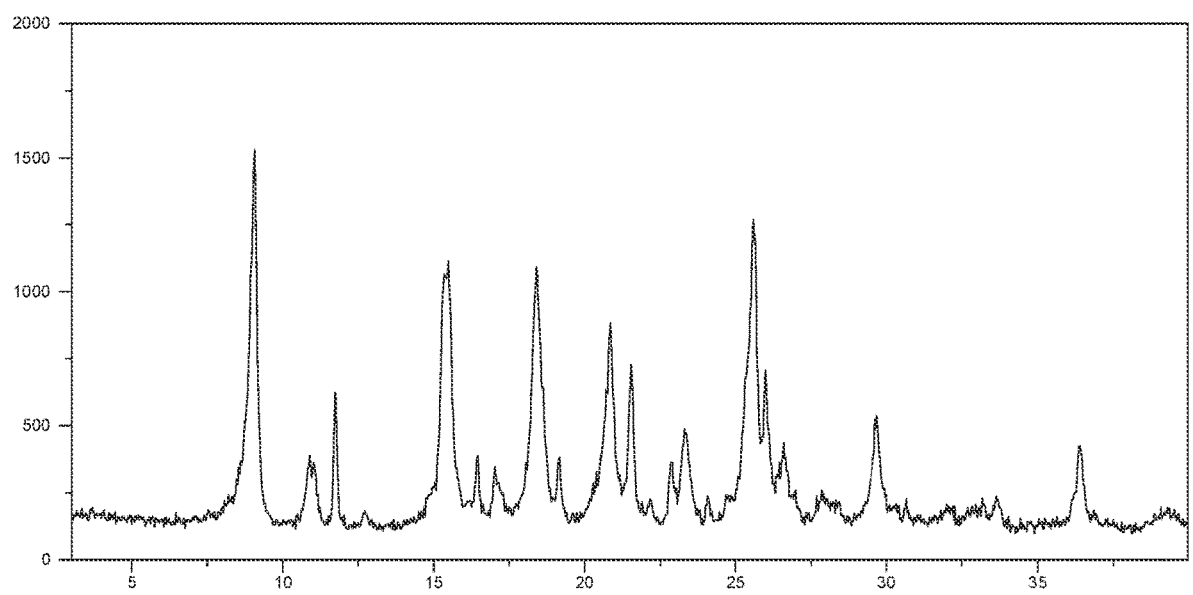
FIG. 14 illustrates an X-ray powder diffraction (XRPD) pattern of Compound (I) HCl salt form 4. X-axis: diffraction angle (°2θ); Y-axis: intensity (counts).
Figure 15:
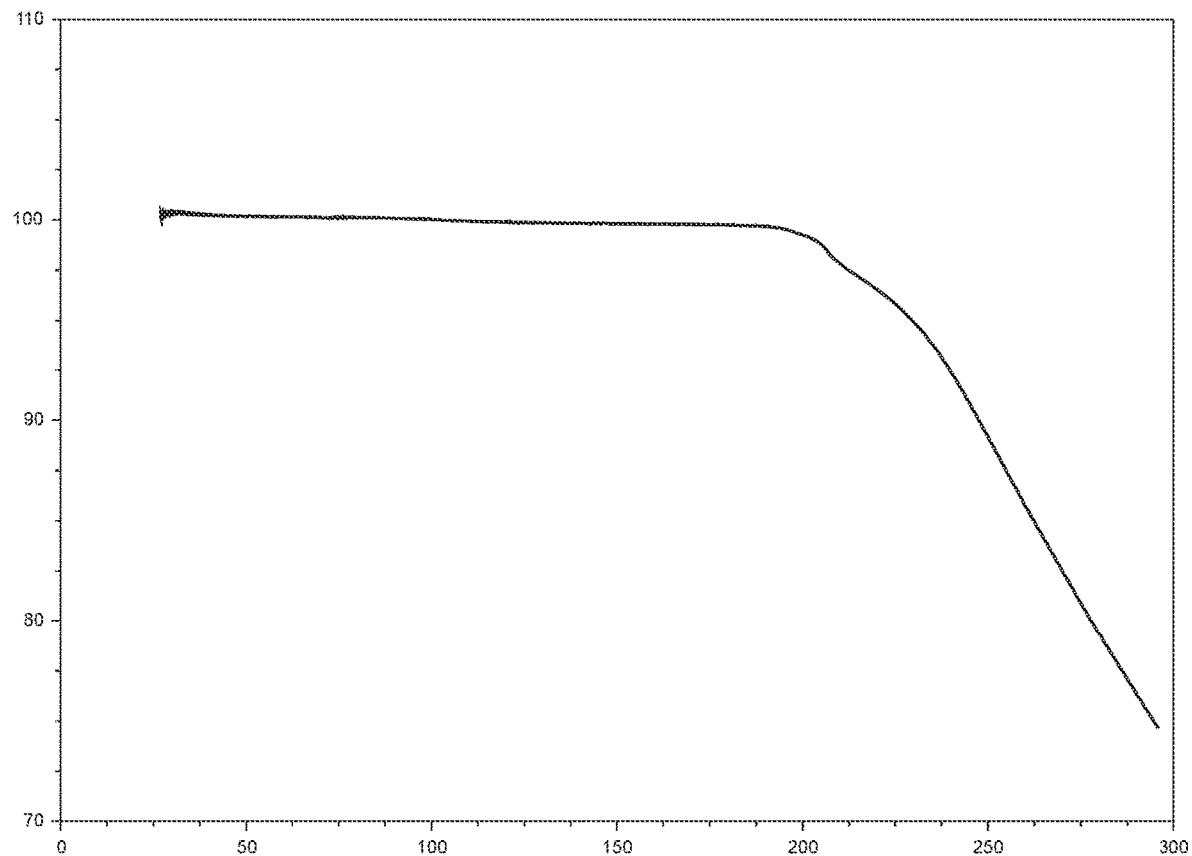
FIG. 15 illustrates a thermo-gravimetric analysis (TGA) thermogram of Compound (I) HCl salt form 4. X-axis: Temperature (° C.); Y-axis: Weight (%).

E14. The crystalline form according to embodiment E1, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 4 having at least one of the following properties:
  a) an X-ray powder diffraction (XRPD) obtained using CuK$_\alpha$ radiation ($\lambda_1$=1.5406 Å, $\lambda_2$=1.5444 Å) showing an XRPD pattern substantially the same as shown in FIG. 14;
  b) an X-ray powder diffraction (XRPD) pattern obtained using CuK$_\alpha$ radiation ($\lambda_1$=1.5406 Å, $\lambda_2$=1.5444 Å) showing characteristic peaks at the following 2θ-angles: 9.05, 11.07, 11.75, 15.31, 18.39, 25.60, 29.67, and 36.40°;
  c) a thermo-gravimetric analysis (TGA) substantially similar to the one set forth in FIG. 15; or
  d) combination thereof.

E15. The crystalline form according to embodiment E14, wherein the crystalline form is 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 4 having a crystal form characterized by an XRPD obtained using CuK$_\alpha$ radiation ($\lambda_1$=1.5406 Å, $\lambda_2$=1.5444 Å) showing peaks at the following 2θ-angles: 9.05, 11.07, 11.75, 15.31, 18.39, 25.60, 29.67, and 36.40°.

E16. A pharmaceutical composition comprising a crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid, or a pharmaceutically acceptable salt, according to any of embodiments E1-E15 and one or more pharmaceutically acceptable carriers or diluents.

E17. A process of manufacturing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 comprising the step of:
  i) providing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate;
  ii) heating 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate to above 150-180° C. at a minimum of 2 minutes.

E18. The process of embodiment E17, wherein step i) comprises the steps of: providing 1-(1-(2-(pyrrolidin-1-yl)-4-(trifluoromethyl)benzyl)-1,8-diazaspiro[4.5]decane-8-carbonyl)-1H-pyrazole-3-carboxylic acid; adding acetone to provide a solution comprising 1-(1-(2-(pyrrolidin-1-yl)-4-(trifluoromethyl)benzyl)-1,8-diazaspiro[4.5]decane-8-carbonyl)-1H-pyrazole-3-carboxylic; maturing the solution comprising 1-(1-(2-(pyrrolidin-1-yl)-4-(trifluoromethyl)benzyl)-1,8-diazaspiro[4.5]decane-8-carbonyl)-1H-pyrazole-3-carboxylic acid.

E19. A process according to embodiment E18, wherein the acetone is added between 5-50° C.

E20. A process according to any one of embodiments E18-E19, wherein the mixture comprising 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate is matured for at least 24 hours, preferably for at least 72 hours.

E21. A process of manufacturing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 comprising the step of:
  i) Providing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1;
  ii) drying crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1 to provide crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1.

E22. The process according to embodiment E21, wherein step i) comprises the steps of providing 1-(1-(2-(pyrrolidin-1-yl)-4-(trifluoromethyl)benzyl)-1,8-diazaspiro[4.5]decane-8-carbonyl)-1H-pyrazole-3-carboxylic acid and adding 1,4-dioxane at room temperature to provide a mixture comprising 1-(1-(2-(pyrrolidin-1-yl)-4-(trifluoromethyl)benzyl)-1,8-diazaspiro[4.5]decane-8-carbonyl)-1H-pyrazole-3-carboxylic acid and stirring the solution at least 24 hours at 0-10° C., preferably at 5° C.

E23. The process according to embodiment E22, wherein the solution is stirred for at least 36 hours, preferably for 48 hours.

E24. A process of manufacturing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 comprising the step of:
  i) providing 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2;
  ii) drying 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2 to provide crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1.

E25. A process according to embodiment E24, wherein step i) comprises the step of providing 1-(1-(2-(pyrrolidin-1-yl)-4-(trifluoromethyl)benzyl)-1,8-diazaspiro[4.5]decane-8-carbonyl)-1H-pyrazole-3-carboxylic acid and adding 1,4-dioxane at room temperature to provide a mixture comprising 1-(1-(2-(pyrrolidin-1-yl)-4-(trifluoromethyl)benzyl)-1,8-diazaspiro[4.5]decane-8-carbonyl)-1H-pyrazole-3-carboxylic acid followed by stirring the solution at least 24 hours at 40-60° C., preferably at 50° C.

E26. The process according to embodiment E25, wherein the mixture is stirred for at least 36 hours, preferably 48 hours.

E27. The process according to any one of embodiments E20 to E26, wherein the drying step is performed in vacuum at room temperature.

E28. The crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid, or a pharmaceutically acceptable salt thereof according to any one of embodiments E1 to E15 for use in the treatment of a disease or disorder selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

E29. A method for the treatment of disease or a disorder selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain; which method comprises the administration of a therapeutically effective amount of the crystalline form of 2-(2-((4-(((1,1,1,3,3,3-hexafluoropropan-2-yl)oxy)carbonyl)piperazin-1-yl)methyl)-5-(trifluoromethyl)phenoxy)-2-methylpropanoic acid, or a pharmaceutically acceptable salt thereof according to any of embodiments E1 to E15 to a patient in need thereof.

E30. Use of the crystalline form of 2-(2-((4-(((1,1,1,3,3,3-hexafluoropropan-2-yl)oxy)carbonyl)piperazin-1-yl)methyl)-5-(trifluoromethyl)phenoxy)-2-methylpropanoic acid, or a pharmaceutically acceptable salt thereof according to any of embodiments E1 to E15 in the manufacture of a medicament for the treatment of disease or a disorder selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

Pharmaceutical Compositions

The above-mentioned compounds or pharmaceutically acceptable salts may be in a composition as the sole active ingredient or in combination with other active ingredients. Additionally, one or more pharmaceutically acceptable carriers or diluents may be in the composition.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragées, pills, lozenges, powders and granules. Where appropriate, they can be prepared with coatings. Oral dosage forms, and in particular tablets, are often preferred by the patients and the medical practitioner due to the ease of administration and the consequent better compliance. For tablets, it is preferable that the active ingredients are crystalline.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, creams, gels, inhalants, dermal patches, implants, etc.

Conveniently, the compounds of the invention are administered in a unit dosage form containing said compounds in an amount of about 0.1 to 500 mg, such as 1 mg, 2 mg, 4 mg, 6 mg 8 mg, 10 mg, 20 mg, 30 mg, 40 mg, 50 mg 100 mg, 150 mg, 200 mg or 250 mg of a compound of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phosphor lipids, fatty acids, fatty acid amines, polyoxyethylene and water. The pharmaceutical compositions formed by combining the compound of the invention and the pharmaceutically acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be a tablet, capsule, or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by compression of the mixture in a conventional tablet machine. Examples of adjuvants or diluents comprise corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

In an embodiment, 1-(1-(2-(pyrrolidin-1-yl)-4-(trifluoromethyl)benzyl)-1,8-diazaspiro[4.5]decane-8-carbonyl)-1H-pyrazole-3-carboxylic acid or a pharmaceutically acceptable salt thereof is provided in an oral solution comprising buffer, benzoic acid, hydroxypropyl betadex, acesulfame potassium, denatonium benzoate, and water.

Conditions for Treatment

Also disclosed herein are methods of treating and/or preventing having a disease or disorder which may benefit from inhibition of MAGL. Disclosed methods include administering a pharmaceutically effective amount of a compound described herein.

Atopic Dermatitis

Atopic Dermatitis (AD), also known as eczema, is a common chronic inflammatory skin disorder associated with dysfunction of the body's immune system. AD affects up to 20% of children but can extend to adulthood affecting up to 3% of adults. In AD the skin becomes extremely itchy. Excessive scratching leads to redness, swelling, cracking, "weeping" clear fluid and crusting of the skin. A functional endocannabinoid signaling system is present in the skin and mediates multiple aspects of skin biology. Third-party studies indicate that CB1 and CB2 receptors are upregulated in atopic dermatitis and that the endocannabinoid system exerts a protective effect in models of skin allergy. In addition, it has been demonstrated that MAGL inhibitors can decrease MAGL activity and increase levels of 2-AG in rodent skin.

In some embodiments, MAGL inhibitors described herein have efficacy in treating atopic dermatitis. In some embodiments, disclosed herein is a method of treating atopic dermatitis in a patient in need thereof, comprising administering to the patient a therapeutically effective amount of Compound (I), or a pharmaceutically acceptable salt or solvate thereof. In some embodiments, disclosed herein is a method of treating atopic dermatitis in a patient in need thereof, comprising administering to the patient a therapeutically effective amount of Compound (I) form 1, Compound (I) form 7, Compound (I) HCl form 2 or Compound (I) HCl form 4.

Fibromyalgia

Fibromyalgia (FM) is a common, chronic, idiopathic condition characterized by diffuse body pain and the presence of pressure allodynia. Several third-party studies of exocannabinoids in FM have indicated activity. For example, measures of pain (e.g., NRS-11, Pain VAS) and the Fibromyalgia Impact Questionnaire (FIQ), which measures limitations in several activities of daily living impacted by FM, have demonstrated activity of drugs in FM clinical trials. In an 8-week, 40-patient study, compared with placebo, an exocannabinoid improved pain measured on a 10 cm VAS, and improved the FIQ domain of anxiety and the FIQ total score.

In some embodiments, MAGL inhibitors described herein have efficacy in treatment of FM. In some embodiments, disclosed herein is a method of treating fibromyalgia in a patient in need thereof, comprising administering to the patient a therapeutically effective amount of Compound (I) form 1, Compound (I) form 7, Compound (I) HCl form 2 or Compound (I) HCl form 4.

Migraine

Migraine is a common episodic disorder of head and facial pain. Migraine attacks can be acutely treated with NSAIDs, acetaminophen, a variety of triptans (e.g., sumatriptan), and antiemetics, but some migraine sufferers have pain unresponsive to existing treatment options. Third party data suggests that endocannabinoid pathways may be relevant in migraine. Inpatients with chronic migraine and probable analgesic-overuse headache, CSF samples showed higher levels of the endocannabinoid palmitoylethanolamide and lower levels of anandamide compared with healthy controls. In addition, patients with a primary diagnosis of migraine headaches found a decrease in the frequency of migraine headaches after initiating marijuana therapy.

In some embodiments, MAGL inhibitors described herein have efficacy in treatment of migraine. In some embodiments, disclosed herein is a method of treating migraine in a patient in need thereof, comprising administering to the patient a therapeutically effective amount of Compound (I) form 1, Compound (I) form 7, Compound (I) HCl form 2 or Compound (I) HCl form 4.

Acute Pain, Inflammatory Pain, Cancer Pain, and Pain Caused by Peripheral Neuropathy MAGL inhibitors have shown efficacy in several rodent models of pain including models of acute pain, inflammatory pain, cancer pain, and pain caused by chemotherapy-induced peripheral neuropathy.

In some embodiments, MAGL inhibitors described herein have efficacy in treatment of Acute Pain, Inflammatory Pain, Cancer Pain, and Pain Caused by Peripheral Neuropathy. In some embodiments, disclosed herein is a method of treating Acute Pain, Inflammatory Pain, Cancer Pain, and Pain Caused by Peripheral Neuropathy in a patient in need thereof, comprising administering to the patient a therapeutically effective amount of Compound (I) form 1, Compound (I) form 7, Compound (I) HCl form 2 or Compound (I) HCl form 4.

Functional Dyspepsia

Functional dyspepsia (FD) is one of the most common gastrointestinal disorders encountered in clinical practice. Several pathophysiological mechanisms have been proposed to underlie symptom generation in FD, including visceral hypersensitivity due to central or peripheral sensitization, low-grade inflammatory states, altered secretion of gastrointestinal hormones, genetic predisposition, and abnormal gastric emptying or accommodation. Third party data supports the hypothesis that the function of the endocannabinoid system is altered in FD patients.

In some embodiments, MAGL inhibitors described herein have efficacy in treatment of functional dyspepsia. In some embodiments, disclosed herein is a method of treating functional dyspepsia in a patient in need thereof, comprising administering to the patient a therapeutically effective amount of Compound (I) form 1, Compound (I) form 7, Compound (I) HCl form 2 or Compound (I) HCl form 4.

Skeletal Muscle Contusion

Skeletal muscle contusion indicates a direct, blunt, compressive force to a muscle. Contusions are one of the most common sports-related injuries. The severity of contusions ranges from simple skin contusions to muscle and bone contusions to internal organ contusions. In third party data, MAGL inhibition demonstrated anti-inflammatory effects in a rat skeletal muscle contusion model.

In some embodiments, MAGL inhibitors described herein have efficacy in treatment of skeletal muscle contusion. In some embodiments, disclosed herein is a method of treating a skeletal muscle contusion in a patient in need thereof, comprising administering to the patient a therapeutically effective amount of Compound (I) form 1, Compound (I) form 7, Compound (I) HCl form 2 or Compound (I) HCl form 4.

Combination Therapies

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is affected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

For example, e.g., for contemplated treatment of pain, a disclosed compound is co-administered with another therapeutic for pain such as an opioid, a cannabinoid receptor ($CB_1$ or $CB_2$) modulator, a COX-2 inhibitor, acetaminophen, and/or a non-steroidal anti-inflammatory agent. Additional therapeutics e.g., for the treatment of pain that are co-administered, include morphine, pregabalin, gabapentin, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

EXPERIMENTAL SECTION

List of Abbreviations

As used above, and throughout the description of the invention, the following abbreviations, unless otherwise indicated, shall be understood to have the following meanings:

t-Bu: tert-butyl
DCM: dichloromethane ($CH_2Cl_2$)
DMF: dimethylformamide
DMSO: dimethylsulfoxide
equiv: equivalent(s)
EtOH: ethanol
EtOAc: ethyl acetate
HPLC: high performance liquid chromatography
i-PrOAc: isopropyl acetate
MS: mass spectroscopy
NMR: nuclear magnetic resonance
MeCN: acetonitrile
2-MeTHF: 2-Methyltetrahydrofuran
MIBK: Methyl isobutyl ketone
MTBE: Methyl Tert-Butyl Ether
TFA: trifluoroacetic acid
TGA: Thermo-gravimetric Analysis
TLC: thin layer chromatography
RT: room temperature
XRPD X-ray powder diffraction Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1: Preparation of Amorphous Compound (I)

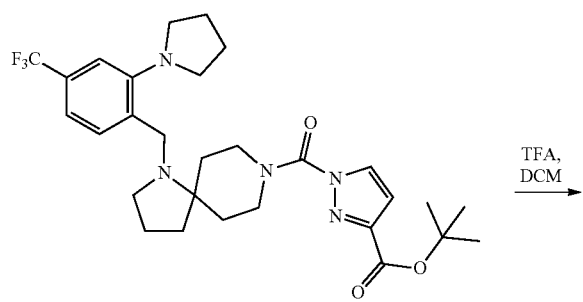

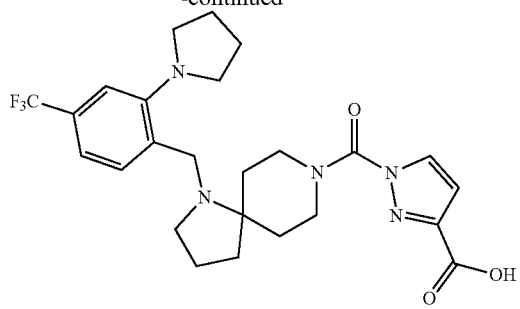

The preparation of compound (I) in amorphous solid form was carried out according to the scheme above and with the following procedure.

Into a 5 L three-necked round-bottom flask, was placed a solution of tert-butyl 1-[(1-[[2-(pyrrolidin-1-yl)-4-(trifluoromethyl)phenyl]methyl]-1,8-diazaspiro[4.5]decan-8-yl)carbonyl]-1H-pyrazole-3-carboxylate (200 g) in DCM (2 L). This was followed by the addition of trifluoroacetic acid (500 mL) dropwise with stirring at 5° C. The resulting solution was stirred for 6 h at room temperature. The resulting mixture was concentrated under vacuum. The residue was dissolved in 3 L of aqueous sodium bicarbonate solution. The resulting solution was extracted with 5×1 L of dichloromethane, the organic layers combined and dried over anhydrous magnesium sulfate. The residue was applied onto a silica gel column with dichloromethane/methanol (1:50-1:5). The crude (150 g) product was re-precipitated from n-Heptane: MTBE in the ratio of 10:1. The obtained 137 g product was pH adjusted to 5-6 with 20% aqueous $KHSO_4$, extracted with DCM, followed by slurrying in n-heptane. An azeotropic distillation in the presence of water is then performed to remove the DCM. This resulted in 100 g of 1-[(1-[[2-(pyrrolidin-1-yl)-4-(trifluoromethyl)phenyl]methyl]-1,8-diazaspiro[4.5]decan-8-yl)carbonyl]-1H-pyrazole-3-carboxylic acid. $^1$H-NMR complies to structure. XRPD showed the resulting solid to be amorphous.

Example 2: Preparation of Compound (I) Form 1

Compound (I) form 1 was obtained using the following procedure.

Figure 2:
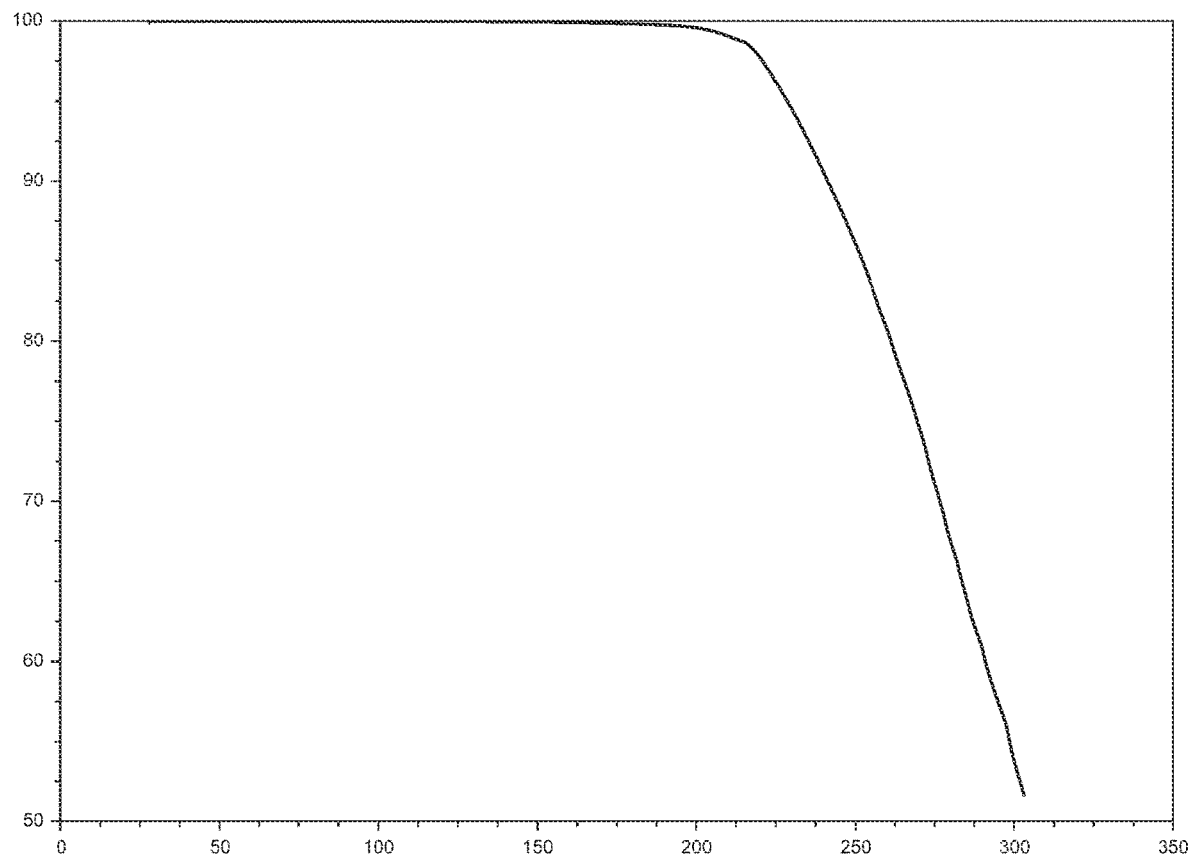
FIG. 2 illustrates a thermo-gravimetric analysis (TGA) thermogram of Compound (I) form 1. X-axis: Temperature (° C.); Y-axis: Weight (%).

Amorphous Compound (I) (1.50 g) was weighed in a 20 ml vial and 7.5 mL (5 vol) ethanol was added at 50° C. and stirred. After 5 minutes, the initial suspension had dissolved to a clear solution. After 20 minutes, a precipitate formed and the sample was cooled to 5° C. at 0.1° C./min and stirred for 24 hours. $^1$H-NMR complies to structure. XRPD analysis revealed the XRPD pattern shown in FIG. 1. TGA thermogram is shown in FIG. 2 and shows that Compound (I) form 1 is unsolvated and unhydrated.

Example 3: Preparation of Compound (I) Form 7

Compound (I) form 7 was obtained using the following procedure.

Figure 4:
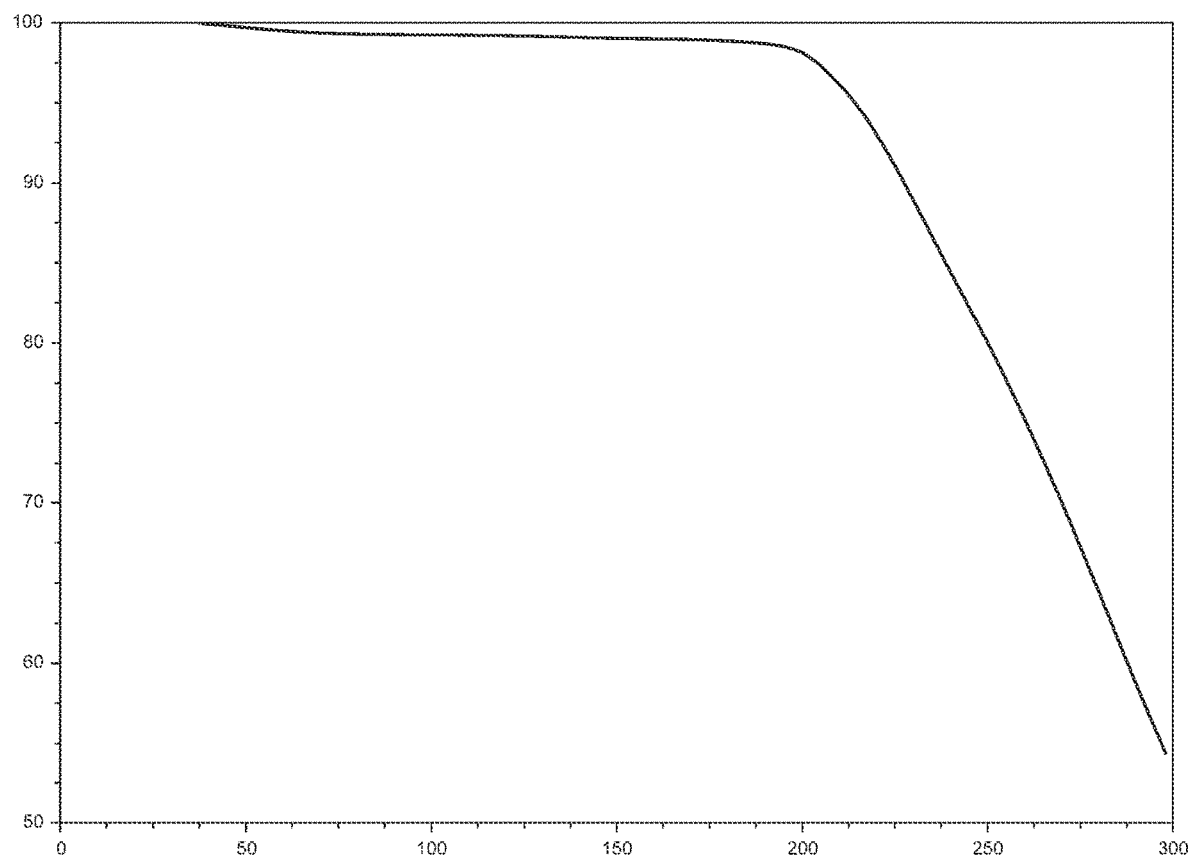
FIG. 4 illustrates a thermo-gravimetric analysis (TGA) thermogram of Compound (I) form 7. X-axis: Temperature (° C.); Y-axis: Weight (%).

1.083 g of amorphous Compound (I), prepared as detailed in Example 1, was weighed in a metal milling vessel and 100 μl of Methanol were added. The sample was milled for 30 minutes at 30 Hz. The sample was left open to ambient conditions overnight to evaporate solvent. $^1$H-NMR complies to structure. XRPD analysis revealed the pattern shown in FIG. 3. TGA thermogram is shown in FIG. 4 and shows that Compound (I) form 7 is unsolvated and unhydrated.

Example 4: Preparation of Compound (I) Acetone Solvate

Compound (I) acetone solvate was obtained using the following procedure.

Figure 6:
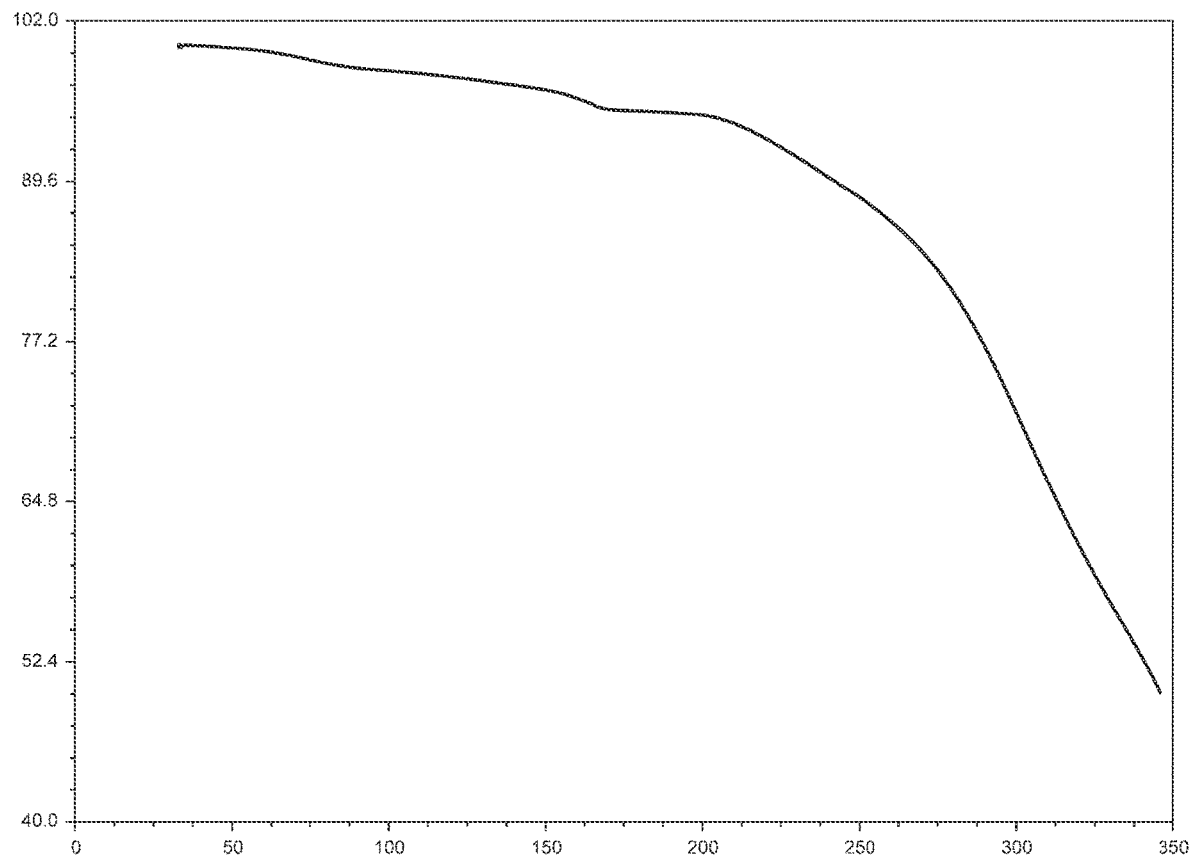
FIG. 6 illustrates a thermo-gravimetric analysis (TGA) thermogram of Compound (I) acetone solvate. X-axis: Temperature (° C.); Y-axis: Weight (%).

Amorphous Compound (I) (100 mg) was weighed into a 2 mL vial and acetone (1 mL, 10 volumes) at 50° C. was added. The solution was left stirring at 50° C. for 30 minutes. The sample was cooled down to 5° C. at 0.1° C./min and matured for 72 hours by cycling the temperature between 5° C. and 50° C. An aliquot of suspension was analysed by XRPD. The suspension was then filtered and dried in a vacuum oven at room temperature for 20 hours. XRPD analysis performed on the wet solid after filtration revealed the XRPD pattern shown in FIG. 5. TGA thermogram is shown in FIG. 6 and shows mass losses consistent with a solvate.

$^1$H-NMR complies with structure and identifies the solvate to be an acetone solvate.

Upon heating Compound (I) acetone solvate for 2 min at 175° C. revealed the XRPD pattern in FIG. 1, indicating Compound (I) acetone solvate transforms into Compound (I) form 1 at elevated temperature.

Example 5: Preparation of Compound (I) 1,4-Dioxane Solvate Form 1

Compound (I) 1,4-dioxane solvate form 1 was obtained using the following procedure.

Amorphous Compound (I) (30 mg) was weighed into a 2 mL vial and 5 volumes (150 μL) 1,4-dioxane were added at room temperature. The mixture was stirred for 20 minutes at room temperature and then stirred at 48 hours at 5° C. The resulting suspension was filtered off at room temperature.

XRPD analysis performed on the wet solid after filtration revealed the XRPD pattern shown in FIG. 7.

XRPD analysis after drying the solid at two hours in a vacuum oven at room temperature revealed an XRPD substantially the same as in FIG. 1, indicating that Compound (I) 1,4-dioxane solvate form 1 transforms into Compound (I) form 1 upon drying.

Example 6: Preparation of Compound (I) 1,4-Dioxane Solvate Form 2

Compound (I) 1,4-dioxane solvate form 1 was obtained using the following procedure.

Amorphous Compound (I) (30 mg) was weighed into a 2 mL vial and 5 volumes (150 μL) 1,4-dioxane were added at room temperature. The mixture was stirred for 20 minutes at room temperature and then stirred at 48 hours at 50° C. The resulting suspension was filtered off at room temperature.

XRPD analysis performed on the wet solid after filtration revealed the XRPD pattern shown in FIG. 8.

XRPD analysis after drying the solid at two hours in a vacuum oven at room temperature revealed an XRPD pattern consistent with FIG. 1, indicating that Compound (I) 1,4-dioxane solvate form 2 transforms into Compound (I) form 1 upon drying.

Example 7: Preparation of Amorphous Compound (I) HCl Salt

Amorphous Compound (I) HCl salt was obtained using the following procedure.

Compound (I) HCl salt Form 2 (800 mg) was weighed into a 20 ml vial and dissolved at in 20 volumes (16 mL) of solvent a 1:3 mixture (v/v) of MeCN/water. The samples were then filtered through a 0.45 μm filter into a new 20 ml vial and 400 μL (equating to 20 mg HCl salt) were aliquoted into HPLC vials. The vial opening was covered in foil and pierced for air holes. The vials were then snap frozen in dry ice/acetone and lyophilised on a freeze dryer overnight. XRPD analysis of the resulting solid showed the samples to be amorphous. $^1$H-NMR analysis showed the sample to be consistent with HCl salt of Compound (I).

Example 8: Preparation of Compound (I) HCl Salt MIBK Solvate

Compound (I) HCl salt form 1 was obtained using the following procedures.

Amorphous Compound (I) HCl salt (50 mg) was slurried in 75 volumes (3.5 mL) MIBK whilst stirring at 50° C. This sample was matured in heat-cool cycles of 50/25° C. (8 hr/cycle) for 3 days. The resulting suspension was filtered into an SPE cartridge with frit at 25° C. under gentle positive pressure to remove excess solvent. The damp solid was isolated by air drying for 10 seconds on Whatman filter paper, then analysing by XRPD.

Figure 9:
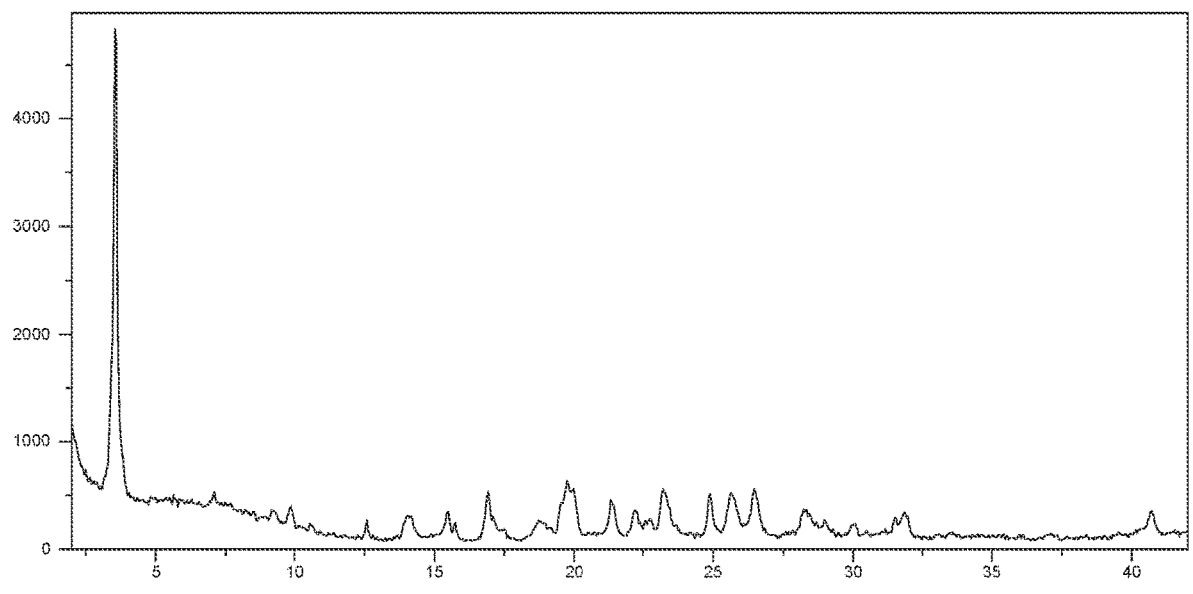
FIG. 9 illustrates an X-ray powder diffraction (XRPD) pattern of Compound (I) HCl salt MIBK solvate. X-axis: diffraction angle (°2θ); Y-axis: intensity (counts).

XRPD analysis of the wet suspension yielded the pattern shown in FIG. 9.

Figure 21:
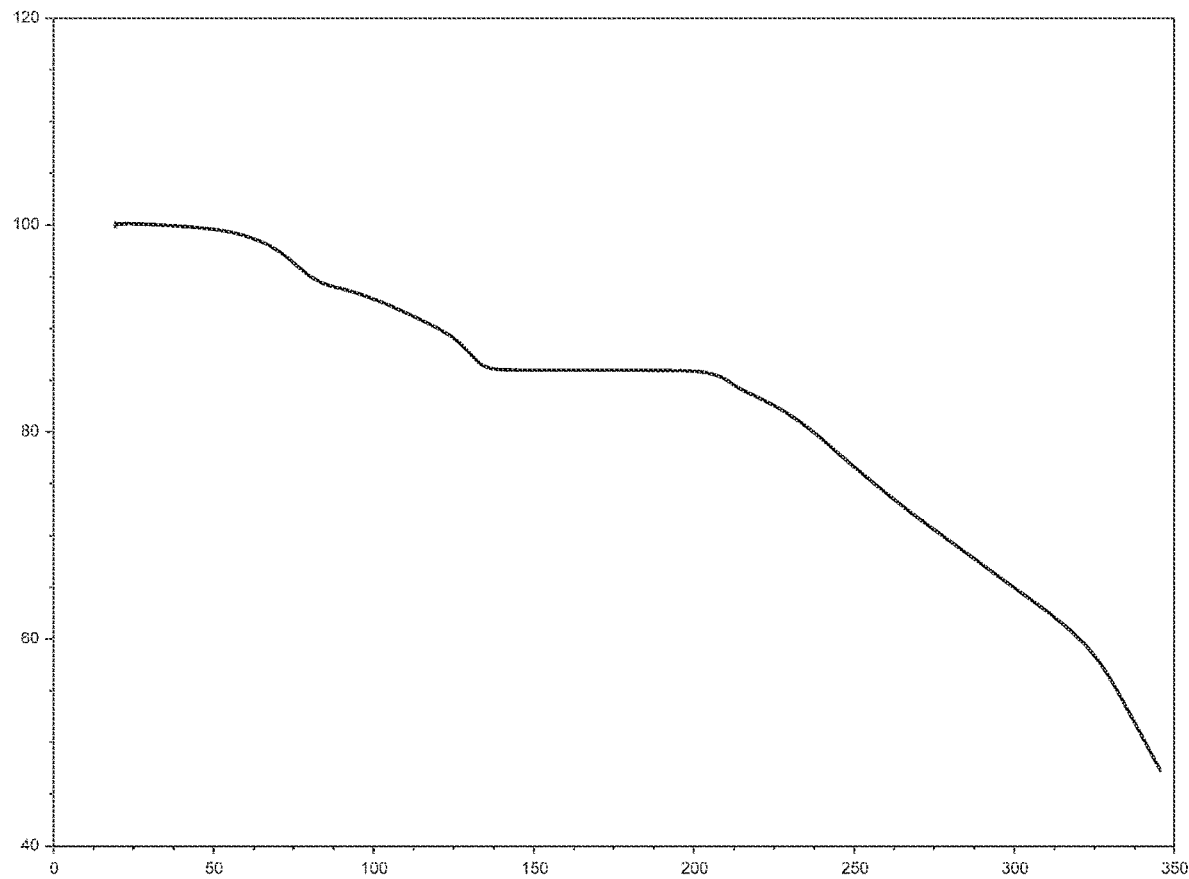
FIG. 21 illustrates a thermo-gravimetric analysis (TGA) thermogram of Compound (I) HCl salt MIBK solvate. X-axis: Temperature (° C.); Y-axis: Weight (%).

TGA analysis (FIG. 21) showed two defined mass losses up to 150° C. that are consistent with the solid form being a solvate.

XRPD analysis after drying the solid revealed an XRPD pattern consistent with FIG. 10, indicating that Compound (I) HCl salt MIBK solvate transforms into Compound (I) HCl salt form 2 upon drying.

Example 9: Preparation of Compound (I) HCl Salt Form 2

Compound (I) HCl salt form 2 was obtained using the following procedures.

To HPLC vials containing 20 mg of amorphous Compound (I) HCl salt were added 10 volumes (200 μL) of ethyl acetate. The resulting suspension was stirred at 500 rpm and matured at 5° C. or 50° C., respectively, for 3-4 days.

XRPD analysis of these samples confirmed Compound (I) HCl salt form 2 is formed under the above conditions.

$^1$H-NMR complies with structure.

Further investigation showed that Compound (I) HCl salt form 2 could also be formed from isopropyl acetate, methyl ethyl ketone and acetone.

Example 10: Preparation of Compound (I) HCl Salt 2-MeTHF Solvate

Compound (I) HCl salt 2-MeTHF solvate was obtained using the following procedure.

Amorphous Compound (I) (30 mg) was weighed into 2 HPLC vials and 2-MeTHF (20 vol) was added. A solution with sticky residue was observed which persisted after stirring at 50° C. for 10 minutes. To the solution ca. 1.1 equivalents of HCl (1 M in THF) was added. A white suspension formed after initial addition of HCl which persisted after 5 minutes stirring at 50° C. The suspension was cooled to 5° C. at 0.1° C./minute and after 24 hours a white suspension was still observed.

After filtration, XRPD analysis of these samples confirmed Compound (I) HCl salt 2-MeTHF solvate is formed under the above conditions.

Figure 13:
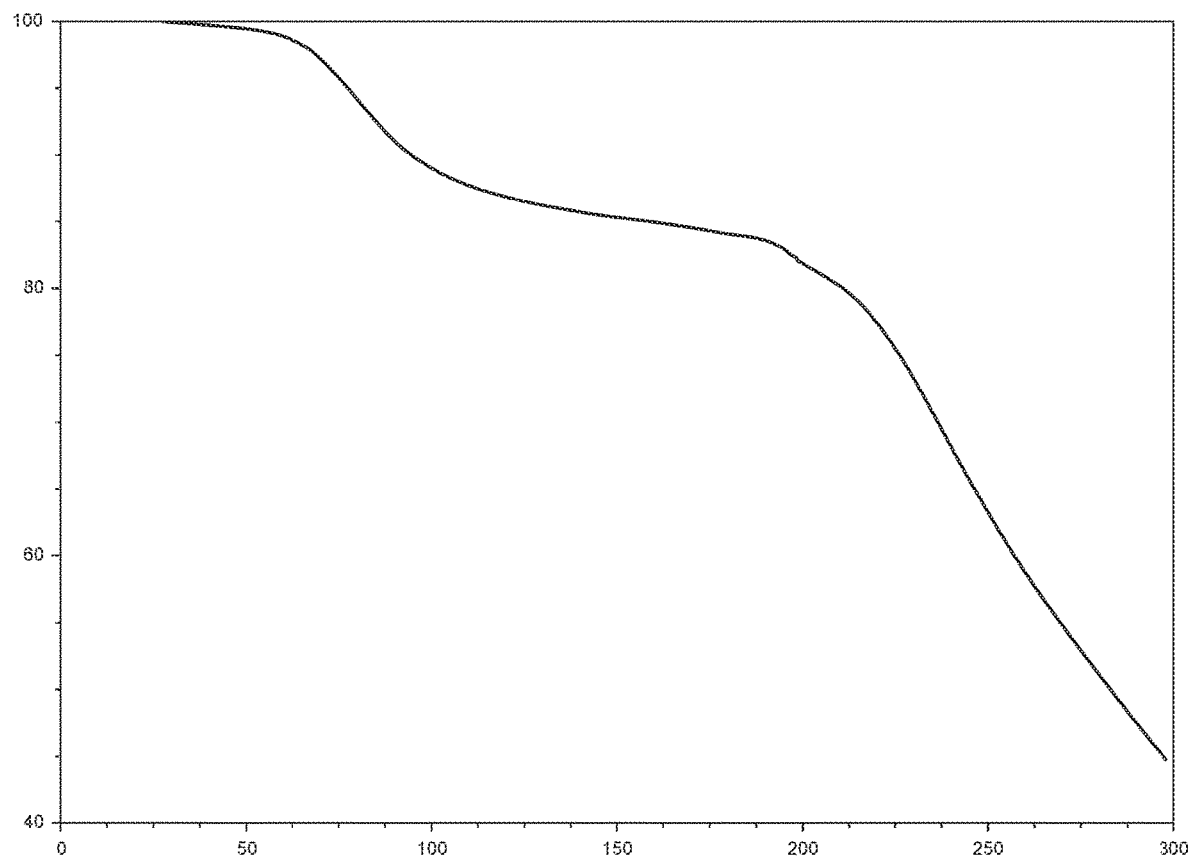
FIG. 13 illustrates a thermo-gravimetric analysis (TGA) thermogram of Compound (I) HCl salt 2-MeTHF solvate. X-axis: Temperature (° C.); Y-axis: Weight (%).

TGA analysis (FIG. 13) showed a mass loss consistent with 1 eq. 2-Me-THF up to 125° C.

Drying of Compound (I) HCl salt 2-MeTHF solvate at 100° C. for 10 minutes with subsequent XRPD analysis showed that the aforementioned 2-MeTHF solvate had transformed into Compound (I) HCl salt form 4 (FIG. 14).

Storing Compound (I) HCl salt 2-MeTHF at 40° C./75% RH for 7 days with subsequent XRPD analysis showed Compound (I) HCl salt 2-MeTHF had transformed into Compound (I) HCl Form 2 (FIG. 10).

Example 11: Preparation of Compound (I) HCl Salt Form 4

Compound (I) HCl salt form 4 was obtained using the following procedure.

4.806 g of Compound (I) form 1 was dissolved in 150 mL 2-MeTHF in a round bottom flask at room temperature.

A mixture of 1.0 g HCl (12 molar, 1.1. equivalents) and 100 mL 2-MeTHF was prepared in a dropping funnel. This mixture was added dropwise over approximately 4 hours.

The resulting suspension was filtered off and the resulting filter cake was washed with 20 mL 2-MeTHF. The product was dried overnight in a vacuum oven at 50° C.

XRPD analysis of these samples confirmed Compound (I) HCl salt form 4 is formed under the above conditions (FIG. 14).

TGA analysis (FIG. 15) showed that the solids formed are an unsolvated form.

Example 12: Preparation of Compound (I) HCl Salt Form 5

Compound (I) HCl salt form 5 was obtained using the following procedure.

500 mg of Compound (I) HCl salt form 2 was dissolved in 35 mL acetonitrile at 55° C.

The solution was cooled to 35° C. over 2 hours.

XRPD analysis of these samples confirmed Compound (I) HCl salt form 5 is formed under the above conditions.

NMR complies with structure.

Example 13: Preparation of Compound (I) HCl Salt Form 6

Compound (I) HCl form 6 was obtained using the following procedure.

Compound (I) HCl salt form 2 (500 mg) was added to a 100 ml round bottom flask, stirred at 25° C., with 700 rpm and charged with MeOH (10 ml, 20 vol). The temperature was raised to 50° C. whilst stirring for 15 minutes. After this time, antisolvent was added in aliquots of 200-400 µl (TBME, 40 ml, 80 vol total) gradually over 10 minutes. The final antisolvent:solvent mixture was 4:1 v/v, and a white suspension resulted. The suspension was stirred at 50° C. for 40 minutes then cooled to 5° C. at 0.1° C./min and held overnight. A suspension remained and was filtered off. The resulting cake was dried under vacuum for 15 minutes at room temperature.

XRPD analysis of the sample confirmed Compound (I) HCl salt form 6 is formed under the above conditions.

Example 14: X-Ray Powder Diffraction (XRPD)

X-ray powder diffractograms shown were recorded using one of three procedures detailed below.

Procedure 1: X-Ray powder diffractograms were measured on a PANalytical X'Pert PRO X-Ray Diffractometer using CuK$_{\alpha 1}$ radiation ($\lambda$=1.5406 Å). The samples were measured in reflection mode in the 2θ-range 3-40° using an X'celerator detector. Samples were run under ambient conditions.

Procedure 2: X-Ray powder diffractograms were collected on a Bruker D8 diffractometer using Cu K$_{\alpha 1}$ radiation. Samples were run under ambient conditions as flat plate specimens. The sample was prepared on a polished, zero-background (510) silicon wafer and rotated in its own plane. Data was collected in the 2θ-range 2-42° with step sizes of 0.05° 2θ and a total collection time of 6.4 min.

Procedure 3: XRPD diffractograms were collected on a PANalytical Empyrean diffractometer using Cu K$_\alpha$ radiation (45 kV, 40 mA) in transmission geometry. Samples were prepared and analysed in either a metal or Millipore 96 well-plate in transmission mode. X-ray transparent film was used between the metal sheets on the metal well-plate and powders (approximately 1-2 mg) were used as received. Data was collected in the 2θ-range 2.5-32° with step sizes of 0.0130° 2θ and total collection time of 2.07 min.

Procedure 4 carried out under non-ambient conditions: For variable temperature (VT-XRPD) experiments the samples were prepared and analysed in an Anton Paar chromed sample holder. A heating/cooling rate of 10° C./min was used. The measurement parameters are as per the standard screening data collection method (detailed in Procedure 3 above). Measurements were taken at the following temperatures: 25, 100, 145, 150, 155, 160, 165, 170, 175, and 25° C.

In Table 1 the characteristic peaks measured for Compound (I) form 1, Compound (I) form 7, Compound (I) acetone solvate, Compound (I) 1,4-dioxane solvate form 1, Compound (I) 1,4-dioxane solvate form 2, Compound (I) HCl salt form 2, and Compound (I) HCl salt form 4 are listed.

Table 1 lists the characteristic peaks measured for the different solid forms of Compound (I) using the above measurement procedures. Diffraction data are indicated ±0.1° 2θ.

TABLE 1

Charateristic XRPD peaks of the compounds of the invention

| Crystalline form | Peaks expressed in degree of diffraction angle [°2θ] | Procedure |
|---|---|---|
| Compound (I) form 1 | 8.60, 10.72, 11.12, 14.17, 15.30, 19.08, 22.70, 24.30 | 1 |
| Compound (I) form 7 | 8.91, 9.20, 12.17, 14. 11, 16.33, 18.46, 19.90 | 2 |
| Compound (I) acetone solvate | 10.19, 11.09, 15.00, 17.86, 19.57, 20.84, 23.74, 31.34 | 3 |
| Compound (I) 1,4-dioxane solvate form 1 | 7.46, 14.64, 15.09, 16.15, 18.72, 19.34, 25.22, 25.92 | 3 |
| Compound (I) 1,4-dioxane solvate form 2 | 6.67, 11.01, 15.23, 16.06, 16.81, 19.39, 19.77, 22.84 | 3 |
| Compound (I) HCl salt form 2 | 4.30, 10.16, 12.85, 15.67, 21.54, 23.08 | 1 |
| Compound (I) HCl salt form 4 | 9.05, 11.07, 11.75, 15.31, 18.39, 25.60, 29.67, 36.40 | 1 |

XRPD Analysis of the Obtained Compounds

XRPD analysis (FIG. 1) of Compound (I) form 1 showed the form to be crystalline.

XRPD analysis (FIG. 3) of Compound (I) form 7 showed the form to be crystalline.

XRPD analysis (FIG. 5) of Compound (I) acetone solvate showed the solvate to be crystalline.

XRPD analysis (FIG. 7) of Compound (I) 1,4-dioxane solvate form 1 showed the solvate form to be crystalline.

XRPD analysis (FIG. 8) of Compound (I) 1,4-dioxane solvate form 2 showed the solvate form to be crystalline.

XRPD analysis (FIG. 9) of Compound (I) HCl salt form 1 showed the salt form to be crystalline.

XRPD analysis (FIG. 10) of Compound (I) HCl salt form 2 showed the salt form to be crystalline.

Figure 12:
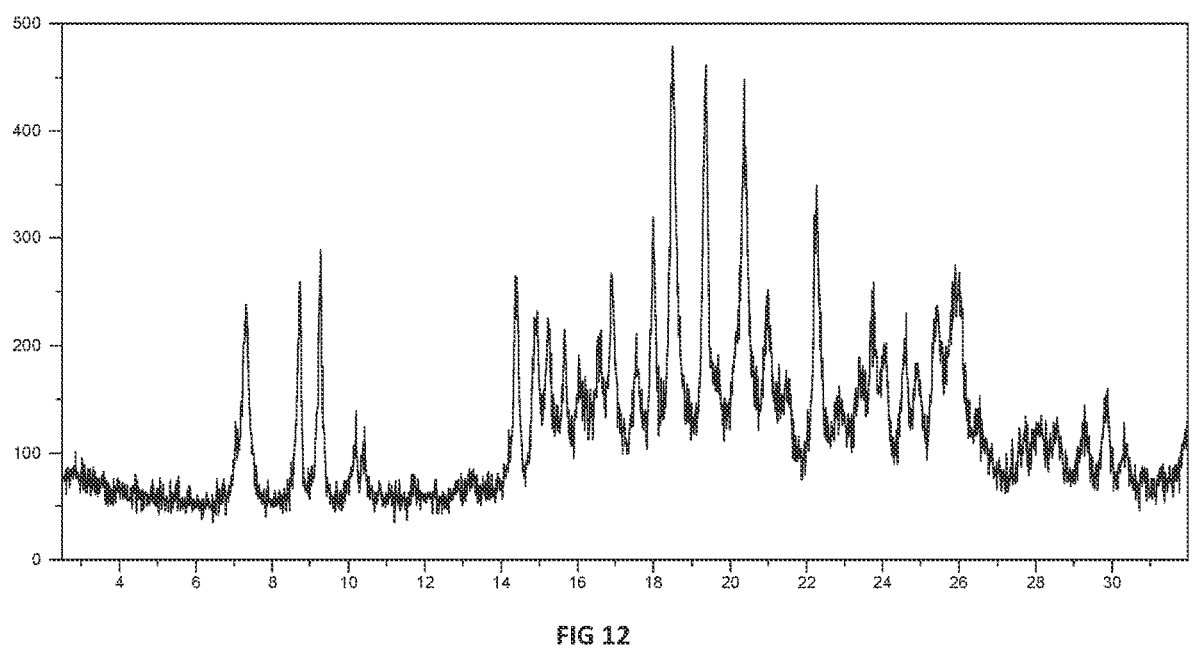
FIG. 12 illustrates an X-ray powder diffraction (XRPD) pattern of Compound (I) HCl salt 2-MeTHF solvate. X-axis: diffraction angle (°2θ); Y-axis: intensity (counts).

XRPD analysis (FIG. 12) of Compound (I) HCl salt 2-MeTHF solvate showed the solvate form to be crystalline.

XRPD analysis (FIG. 14) of Compound (I) HCl salt form 4 showed the salt form to be crystalline.

Figure 16:
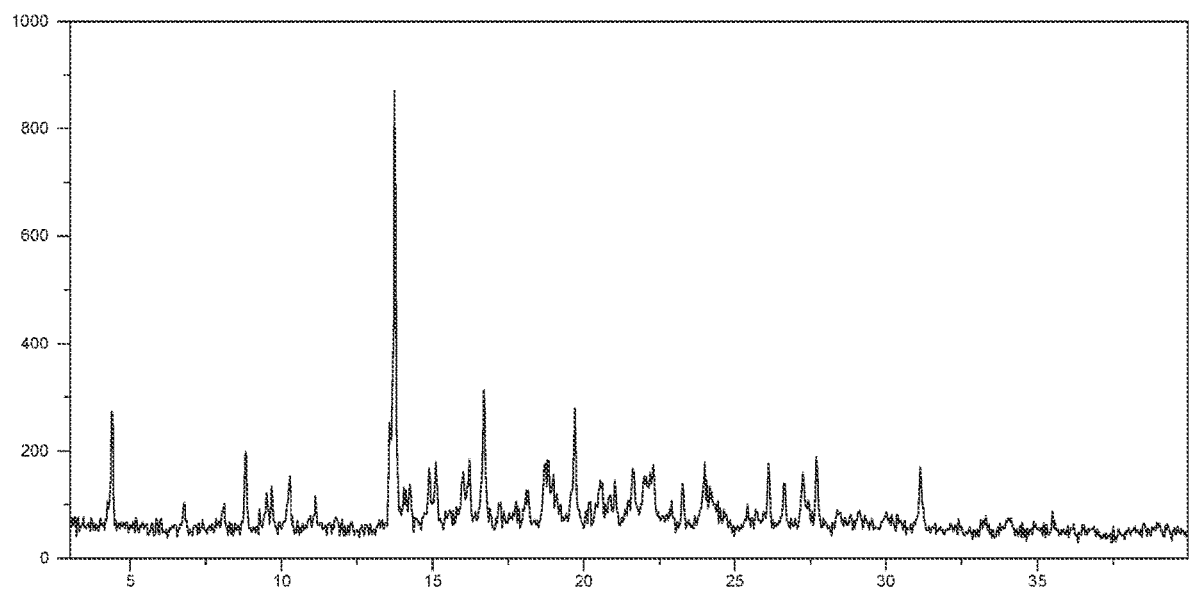
FIG. 16 illustrates an X-ray powder diffraction (XRPD) pattern of Compound (I) HCl salt form 5. X-axis: diffraction angle (°2θ); Y-axis: intensity (counts).

XRPD analysis (FIG. 16) of Compound (I) HCl salt form 5 showed the salt form to be crystalline.

Figure 18:
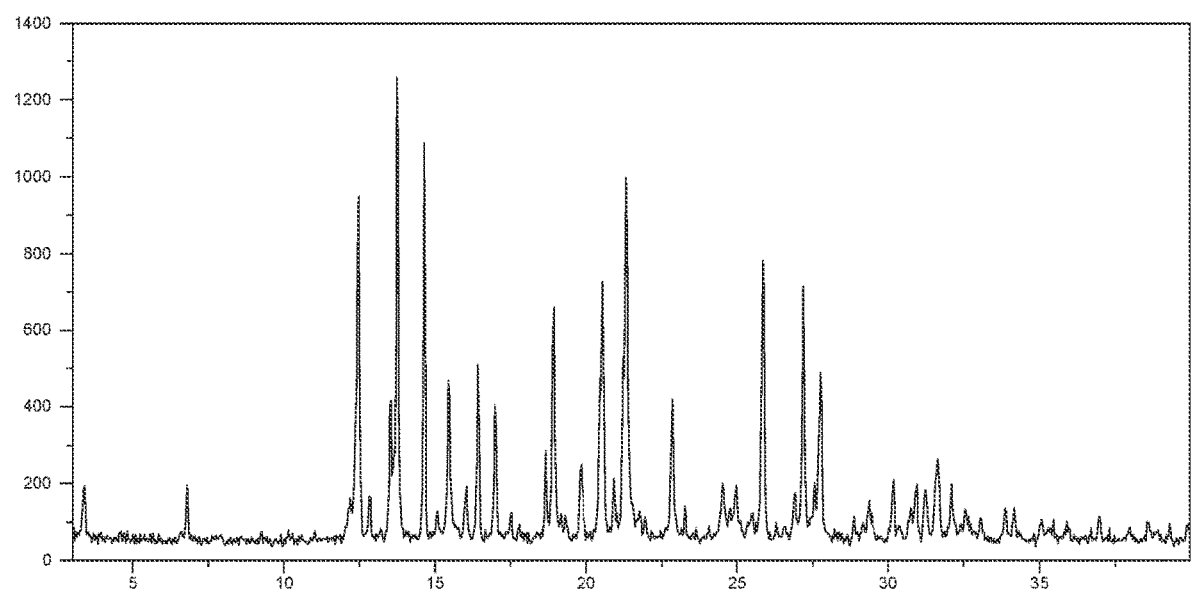
FIG. 18 illustrates an X-ray powder diffraction (XRPD) pattern of Compound (I) HCl salt form 6. X-axis: diffraction angle (°2θ); Y-axis: intensity (counts).

XRPD analysis (FIG. 18) of Compound (I) HCl salt form 6 showed the salt form to be crystalline.

Example 15: Thermo-Gravimetric Analysis (TGA)

Thermo gravimetric analysis (TGA) was measured using a TA-instruments Discovery TGA or a TA-instruments Q500. 1-10 mg sample is heated 10° C./min in an open pan under nitrogen flow.

TGA analysis (FIG. 2) of Compound (I) form 1 showed the form to be unsolvated and unhydrated.

TGA analysis (FIG. 4) of Compound (I) form 7 showed the form to be unsolvated and unhydrated.

TGA analysis (FIG. 6) of Compound (I) acetone solvate showed two defined mass losses of 1.8% up to 80° C. and a further 3.2% up to 175° C., therefore indicating that the form is a solvate.

TGA analysis (FIG. 13) of Compound (I) HCl salt 2-MeTHF solvate showed a defined mass loss of 13.5% up to 125° C., therefore indicating that the form is a solvate.

TGA analysis (FIG. 15) of Compound (I) HCl salt form 4 showed the form to be unsolvated and unhydrated.

Figure 17:
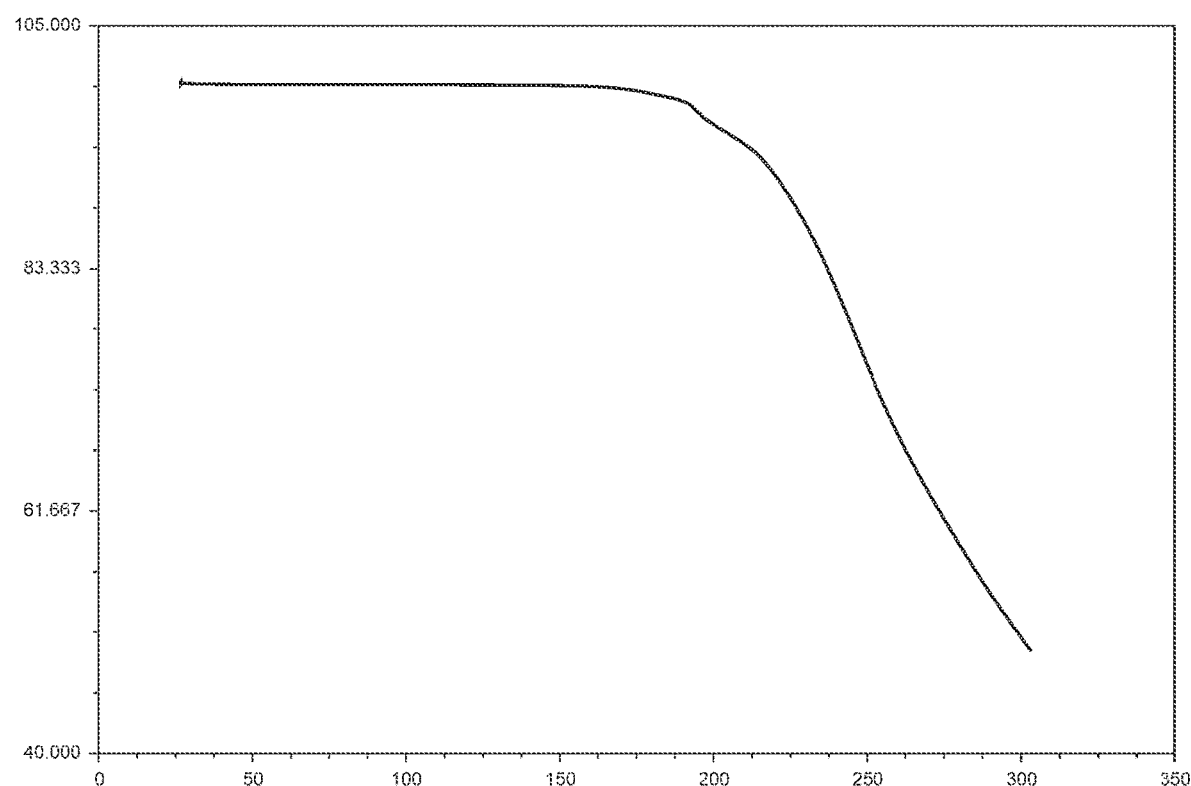
FIG. 17 illustrates a thermo-gravimetric analysis (TGA) thermogram of Compound (I) HCl salt form 5. X-axis: Temperature (° C.); Y-axis: Weight (%).

TGA analysis (FIG. 17) of Compound (I) HCl salt form 5 showed the form to be unsolvated and unhydrated.

Figure 19:
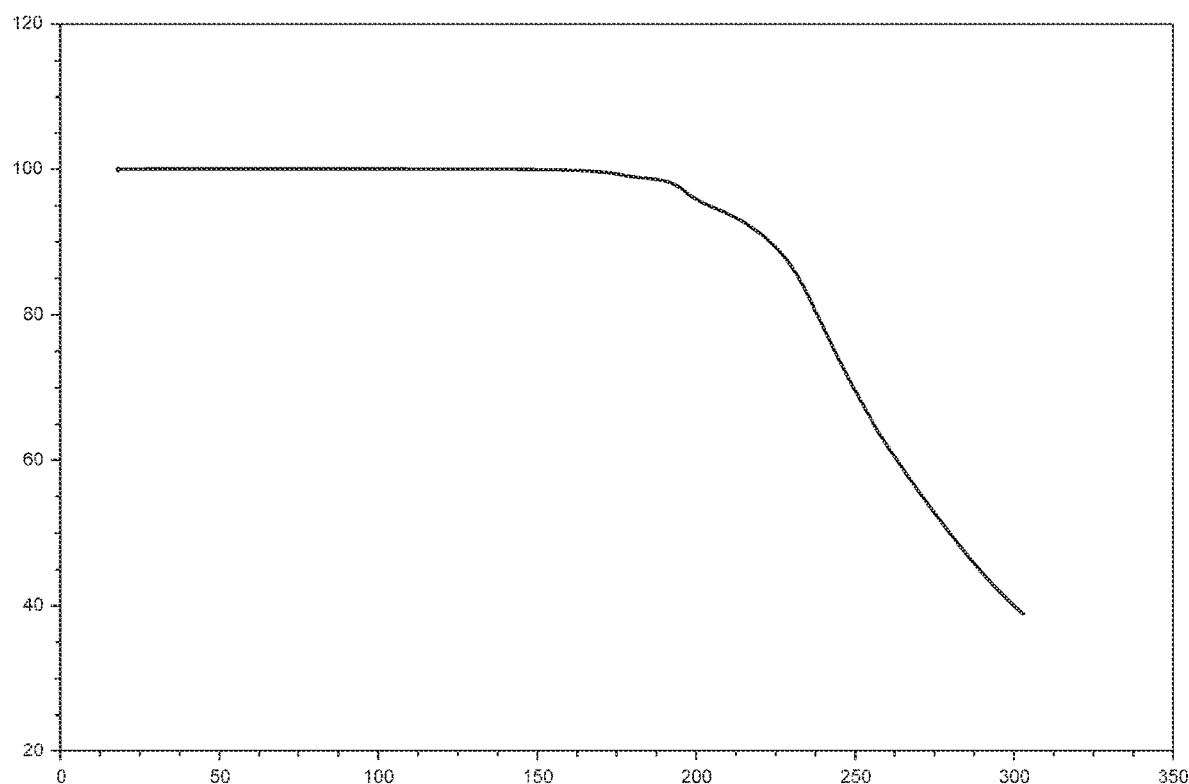
FIG. 19 illustrates a thermo-gravimetric analysis (TGA) thermogram of Compound (I) HCl salt form 6. X-axis: Temperature (° C.); Y-axis: Weight (%).
Figure 20:
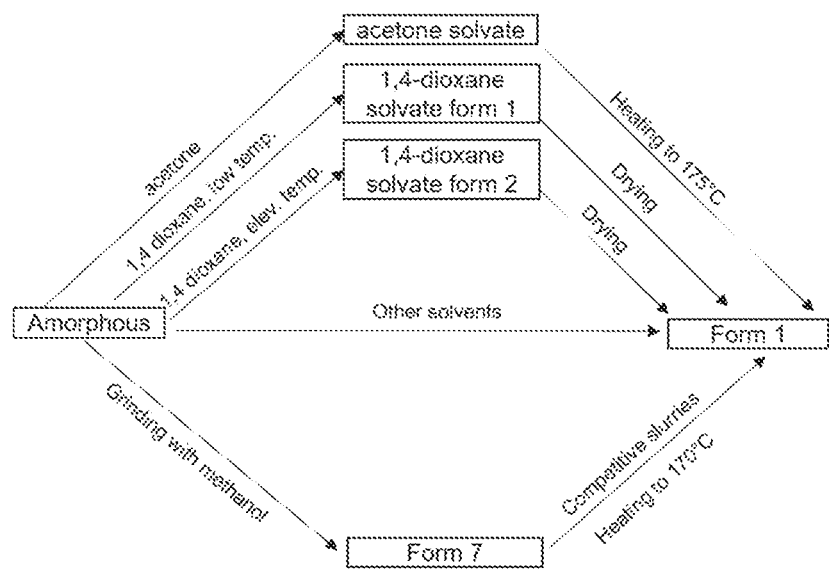
FIG. 20 illustrates an overview of the manufacture of Compound (I) form 1.

TGA analysis (FIG. 19) of Compound (I) HCl salt form 6 showed the form to be unsolvated and unhydrated.

Example 16: Procedures Used for Dynamic Vapor Sorption (DVS) Measurements

Dynamic vapour sorption (DVS) was measured using a SMS DVS Intrinsic moisture sorption analyser changing the relative humidity from 0% RH to 90% RH. The sample temperature was maintained at 25° C. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change of the sample as a function of % RH was constantly monitored by a balance.

Typically, 5-30 mg of sample was placed in a tared mesh stainless steel basket under ambient conditions. The sample was loaded and unloaded at 40% RH and 25° C. (typical room conditions). DVS analysis of Compound (I) form 1 showed the form to be largely non-hygroscopic with water uptake of <1% up to 90% RH. XRPD analysis after DVS analysis confirmed the solid form was still Compound (I) form 1.

DVS analysis of Compound (I) form 7 showed the form to be moderately hygroscopic with water uptake of ~6% up to 90% RH. XRPD analysis after DVS analysis confirmed the solid form was still Compound (I) form 7.

DVS analysis of Compound (I) HCl form 2 showed the form to be slightly hygroscopic with water uptake of 0.5% wt up to 90% RH.

DVS analysis of Compound (I) HCl form 4 showed the form to be slightly hygroscopic with water uptake of 1.4% wt up to 90% RH.

DVS analysis of Compound (I) HCl form 5 showed the form to be moderately hygroscopic with water uptake of 9.2% wt up to 90% RH.

DVS analysis of Compound (I) HCl form 6 showed the form to be moderately hygroscopic with water uptake of 3.1% wt up to 90% RH.

Example 17: $^1$H NMR of Crystalline Forms of Compound (I)

$^1$H NMR spectra were collected on a Bruker 400 MHz instrument equipped with an auto sampler and controlled by a DRX400 console. Samples were prepared in DMSO-d6 solvent, unless otherwise stated.

Example 18: Competitive Slurry Experiments Between Compound (I) Form 1 and Compound (I) Form 7

The relative thermodynamic stability of Compound (I) form 1 and Compound (I) form 7 was elucidated using competitive slurry experiments as detailed in the following.

Step 1: Compound (I) form 1 (150 mg) and Compound (I) form 7 (150 mg) were mixed in a 20 mL vial. 40 mg (each) of this physical mixture was placed into six 2 mL vials.

Step 2: Using the remaining 60 mg of the physical mixture, saturated solutions with methanol and ethanol, respectively, were produced. The saturated solutions were filtered off.

Step 3: 10 volumes (600 µL) of each saturated solution were added to each of the six 2 mL vials mentioned in step 1.

Step 4: One vial for each solvent was kept at 5° C., room temperature and 50° C. for one week.

XRPD analysis carried out on the solids yielded a pattern substantially similar to FIG. 1 for all six vials.

The result of this experiment indicates that Compound (I) form 1 is more thermodynamically stable than Compound (I) form 7 at all temperatures tested. This is evident from the observation that Compound (I) form 7 transforms into Compound (I) form 1 at all temperatures tested. Accordingly, Compound (I) form 1 is more thermodynamically stable than Compound (I) form 7 at standard storage temperatures, i.e. 5-50° C.

Example 19: Variable Temperature XRPD Analysis of Compound (I) Form 7

Compound (I) form 7 obtained using the procedure detailed in Example 2 was subjected to variable temperature X-ray powder diffraction (VT-XRPD), as described in Example 10 ("Procedure 3 under non-ambient conditions").

This XRPD analysis showed conversion from Compound (I) form 7 to Compound (I) form 1 beginning at 160° C. At 170° C. exclusively Compound (I) form 1 was obtained. Mixed forms 7 and 1 were observed between 160° C. and 170° C. This indicates that Compound (I) form 7 recrystallizes into Compound (I) form 1 at these elevated temperatures.

Example 20: Competitive Slurry Experiments Between Different Forms of Compound (I) HCl Salt Competitive slurry experiments between different form of Compound (I) HCl salt were performed to elucidate the relative thermodynamic stability between unsolvated crystalline forms of interest.

To this end, saturated solutions in different solvents were prepared in the following way: Compound (I) HCl salt form 2 (HCl salt, 50-500 mg, depending on solvent mixture) was weighed into 4 ml vials and to each sample was added 1.2-2 ml of solvent. The resulting slurries were stirred for 3 hours to approach equilibrium conditions at either 5 or 50° C., 500 rpm. The following solvents and solvent combinations were utilized: EtOAc, MIBK, THF, MeCN, MeOH, and Acetone. The samples were then filtered using a 0.45 m filter and the resulting saturated solutions (with respect to Compound (I) HCl salt form 2) were used in the competitive slurry experiments as detailed in the next paragraph.

A separate dry powder mixture of Compound (I) HCl salt form 2, 4, 5 and 6 (at least 120 mg each) was prepared. This dry powder mixture was mixed in a gyroscopic Turbula mixer for 2 hours. Then 50 mg aliquots of the mixture were weighed into HPLC vials and 0.5 mL of the above saturated solutions were added. The resulting suspensions were then stirred for 7 days.

The above competitive slurries were sampled after 1 and 7 days. The samples taken after 1 day were air dried and analyzed with XRPD. The samples taken after 7 days were first analyzed in wet state (covered with a Kapton film) in the XRPD and then subjected to air drying and analyzed again. Table 2 presents an overview of the XRPD results gained in this way.

TABLE 2

Overview of XRPD results from competitive slurry experiments performed with different forms of Compound (I) HCl salt

| Temp. (° C.) | Solvent mixture | XRPD 'dry' after 1 day | XRPD 'wet' (Kapton film) after 7 days | XRPD 'dry' after 7 days |
|---|---|---|---|---|
| 5 | EtOAc | HCl salt Form 2 | metastable solvate | HCl salt Form 2 |
| 5 | MIBK | HCl salt MIBK solvate | metastable solvate | HCl salt MIBK solvate |
| 5 | THF | HCl salt Form 4 | metastable solvate | HCl salt Form 4 |
| 5 | MeCN | HCl salt Form 5 | metastable solvate | HCl salt Form 5 |
| 5 | MeOH | HCl salt Form 2 + HCl salt Form 6 | metastable solvate | HCl salt Form 2 + HCl salt Form 6 |
| 5 | Acetone | HCl salt Form 4 | metastable solvate | HCl salt Form 4 |
| 50 | EtOAc | HCl salt Form 2 | metastable solvate | HCl salt Form 2 |
| 50 | MIBK | HCl salt MIBK solvate | metastable solvate | HCl salt MIBK solvate |
| 50 | THF | HCl salt Form 4 | metastable solvate | HCl salt Form 4 |
| 50 | MeCN | HCl salt Form 5 | metastable solvate | HCl salt Form 5 |
| 50 | MeOH | HCl salt Form 2 + HCl salt Form 6 | metastable solvate | HCl salt Form 2 + HCl salt Form 6 |
| 50 | Acetone | HCl salt Form 2 | metastable solvate | HCl salt Form 2 |

Surprisingly, different unsolvated forms and mixtures of forms of Compound (I) HCl salt result from different solvent mixtures, even after extended times at these competitive slurry conditions. Those skilled in the art know that such a result is only possible if solvates exist in the different solvent environments. Otherwise, if no solvates are involved, one would expect that either a mixture of forms results after slurrying (if the kinetics of conversion are slow) or that the same pure crystalline form appears in all solvents if the conversion kinetics permit this. However, with the involvement of solvates it is possible (and indeed likely) that the solvated crystal species represents the most stable crystalline species in a given environment. The results summarized in Table 2, are therefore the result of a surprisingly complex solid form landscape that must involve solvates. Upon close inspection of XRPD data gained on wet powder samples, evidence that the formation of the unsolvated Compound (I) HCl salt forms (form 2, form 4, form 5 and form 6) proceeds through metastable solvates can be identified. This shows that, while the solvates exist in a given solvent environment and are stable in this environment, they readily desolvate under mild drying conditions (drying at room conditions). Further evidence for this behavior was found in the wet samples analyzed in XRPD (second column from the right), where additional peaks on the powder patterns for Form 4, Form 5 and Form 6 were observed that disappear upon drying the samples.

Example 21: Overview of Compound (I) HCl Forms and their Physical Properties To further elucidate differences between the hydrochloride salt forms, their stability at accelerated conditions and their hygroscopicity was measured. The data are summarized in Table 3 together with the observations reported in Example 20. Those skilled in the art see that Compound (I) HCl salt form 2 and form 4 show superior stability over Compound (I) HCl salt form 5 and form 6 and would therefore be preferable for development. Compound (I) HCl salt form 2 shows the lowest water uptake which further points at the form being the most preferable among the identified forms of Compound (I) HCl salt.

TABLE 3

Overview of Compound (I) HCl forms and their physical properties

| Compound (I) HCl salt | Tentative assignment | Hygroscopicity in DVS | Stability at elevated conditions | Other comments |
|---|---|---|---|---|
| Form 2 | Non-solvated | Slightly hygroscopic (0.5 wt % uptake at 90% RH) | No change | Evidence that form originates from metastable solvate |
| Form 4 | Non-solvated | Slightly hygroscopic (1.4 wt % uptake at 90% RH) | No change | Evidence that form originates from metastable solvate |
| Form 5 | Non-solvated | Moderately hygroscopic (9.2 wt % uptake at 90% RH) | Deliquesces at 25° C./ 97% RH | Evidence that form originates from metastable solvate |
| Form 6 | Non-solvated | Moderately hygroscopic (3.1 wt % uptake at 90% RH) | Partial conversion to Form 2 on heating + variable humidity | Evidence that form originates from metastable solvate |

We claim:

1. A crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 having a crystal form characterized by an XRPD obtained using $CuK_{\alpha 1}$ radiation (λ=1.5406 Å) showing peaks at the following 2θ-angles: 8.60°, 10.72°, 11.12°, 14.17°, 15.30°, 19.08°, 22.70°, and 24.30°.

2. A crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid form 7 having a crystal form characterized by an XRPD obtained using $CuK_{\alpha 1}$ radiation (λ=1.5406 Å) showing peaks at the following 2θ-angles: 8.91°, 9.20°, 12.17°, 14.11°, 16.33°, 18.46°, and 19.90°.

3. A crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate having a crystal form characterized by an XRPD obtained using $CuK_{\alpha}$ radiation ($\lambda_1$=1.5406 Å, $\lambda_2$=1.5444 Å) showing peaks at the following 2θ-angles: 10.19°, 11.09°, 15.00°, 17.86°, 19.57°, 20.84°, 23.74°, 31.34°.

4. A crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1 having a crystal form characterized by an XRPD obtained using $CuK_{\alpha}$ radiation ($\lambda_1$=1.5406 Å, $\lambda_2$=1.5444 Å) showing peaks at the following 2θ-angles: 7.46°, 14.64°, 15.09°, 16.15°, 18.72°, 19.34°, 25.22°, 25.92°.

5. A crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2 having a crystal form characterized by an XRPD obtained using $CuK_{\alpha}$ radiation ($\lambda_1$=1.5406 Å, $\lambda_2$=1.5444 Å) showing peaks at the following 2θ-angles: 6.67°, 11.01°, 15.23°, 16.06°, 16.810, 19.39°, 19.77°, 22.84°.

6. A crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 2 having a crystal form characterized by an XRPD obtained using $CuK_{\alpha 1}$ radiation (λ=1.5406 Å) showing peaks at the following 2θ-angles: 4.30°, 10.16°, 12.85°, 15.67°, 21.54°, and 23.08°.

7. A crystalline form of 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 4 having a crystal form characterized by an XRPD obtained using $CuK_{\alpha}$ radiation ($\lambda_1$=1.5406 Å, $\lambda_2$=1.5444 Å) showing peaks at the following 2θ-angles: 9.05°, 11.07°, 11.75°, 15.31°, 18.39°, 25.60°, 29.67°, 36.40°.

8. A process of manufacturing the crystalline form of claim 1, comprising the steps of:
i) providing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate; and
ii) heating 1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate to above 150-180° C. at a minimum of 2 minutes.

9. A process of manufacturing the crystalline form of claim 1, comprising the steps of:
i) providing crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1; and
ii) drying crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1 to provide crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1.

10. A process of manufacturing crystalline form of claim 1, comprising the steps of:
i) providing 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2; and
ii) drying 1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2 to provide crystalline 1-(1-(2-(pyrrolidin-1-yl)-4-(trifluoromethyl)benzyl)-1,8-diazaspiro[4.5]decane-8-carbonyl)-1H-pyrazole-3-carboxylic acid form 1.

11. A pharmaceutical composition comprising the crystalline form of claim 1, and one or more pharmaceutically acceptable carriers or diluents.

12. A method of treating a disease or a disorder in a patient in need thereof, comprising administering to the patient a therapeutically effective amount of the crystalline form of claim 1, wherein the disease or disorder is selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

13. A pharmaceutical composition comprising the crystalline form of claim 3, and one or more pharmaceutically acceptable carriers or diluents.

14. A method of treating a disease or a disorder in a patient in need thereof, comprising administering to the patient a therapeutically effective amount of the crystalline form of claim 3, wherein the disease or disorder is selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

15. A pharmaceutical composition comprising:
1-(1-(2-(pyrrolidin-1-yl)-4-(trifluoromethyl)benzyl)-1,8-diazaspiro[4.5]decane-8-carbonyl)-1H-pyrazole-3-carboxylic acid form 1 having a crystal form characterized by an XRPD obtained using $CuK_{\alpha 1}$ radiation (λ=1.5406 Å) showing peaks at the following 2θ-angles: 8.60°, 10.72°, 11.12°, 14.17°, 15.30°, 19.08°, 22.70°, and 24.30°;

1-(1-(2-(pyrrolidin-1-yl)-4-(trifluoromethyl)benzyl)-1,8-diazaspiro[4.5]decane-8-carbonyl)-1H-pyrazole-3-carboxylic acid form 7 having a crystal form characterized by an XRPD obtained using CuK$_{α1}$ radiation (λ=1.5406 Å) showing peaks at the following 2θ-angles: 8.91°, 9.20°, 12.17°, 14.11°, 16.33°, 18.46°, and 19.90°;

1-(1-(2-(pyrrolidin-1-yl)-4-(trifluoromethyl)benzyl)-1,8-diazaspiro[4.5]decane-8-carbonyl)-1H-pyrazole-3-carboxylic acid acetone solvate having a crystal form characterized by an XRPD obtained using CuK$_α$ radiation (λ$_1$=1.5406 Å, λ$_2$=1.5444 Å) showing peaks at the following 2θ-angles: 10.19°, 11.09°, 15.00°, 17.86°, 19.57°, 20.84°, 23.74°, 31.34°;

1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 1 having a crystal form characterized by an XRPD obtained using CuK$_α$ radiation (λ$_1$=1.5406 Å, λ$_2$=1.5444 Å) showing peaks at the following 2θ-angles: 7.46°, 14.64°, 15.09°, 16.15°, 18.72°, 19.34°, 25.22°, 25.92°;

1-(1-(2-(pyrrolidin-1-yl)-4-(trifluoromethyl)benzyl)-1,8-diazaspiro[4.5]decane-8-carbonyl)-1H-pyrazole-3-carboxylic acid 1,4-dioxane solvate form 2 having a crystal form characterized by an XRPD obtained using CuK$_α$ radiation (λ$_1$=1.5406 Å, λ$_2$=1.5444 Å) showing peaks at the following 2θ-angles: 6.67°, 11.010, 15.23°, 16.06°, 16.810, 19.39°, 19.77°, 22.84°;

1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 2 having a crystal form characterized by an XRPD obtained using CuK$_{α1}$ radiation (λ=1.5406 Å) showing peaks at the following 2θ-angles: 4.30°, 10.16°, 12.85°, 15.67°, 21.54°, and 23.08°; or 1-(1-(2-(pyrrolidin-1-yl)-4-(trifluoromethyl)benzyl)-1,8-diazaspiro[4.5]decane-8-carbonyl)-1H-pyrazole-3-carboxylic acid HCl salt form 4 having a crystal form characterized by an XRPD obtained using CuK$_α$ radiation (λ$_1$=1.5406 Å, λ$_2$=1.5444 Å) showing peaks at the following 2θ-angles: 9.05°, 11.07°, 11.75°, 15.31°, 18.39°, 25.60°, 29.67°, 36.40°;

or any combination thereof; and one or more pharmaceutically acceptable carriers or diluents.

16. A pharmaceutical composition comprising the crystalline form of claim 2, and one or more pharmaceutically acceptable carriers or diluents.

17. A method of treating a disease or a disorder in a patient in need thereof, comprising administering to the patient a therapeutically effective amount of the crystalline form of claim 2, wherein the disease or disorder is selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

18. A pharmaceutical composition comprising the crystalline form of claim 4, and one or more pharmaceutically acceptable carriers or diluents.

19. A method of treating a disease or a disorder in a patient in need thereof, comprising administering to the patient a therapeutically effective amount of the crystalline form of claim 4, wherein the disease or disorder is selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

20. A pharmaceutical composition comprising the crystalline form of claim 5, and one or more pharmaceutically acceptable carriers or diluents.

21. A method of treating a disease or a disorder in a patient in need thereof, comprising administering to the patient a therapeutically effective amount of the crystalline form of claim 5, wherein the disease or disorder is selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

22. A pharmaceutical composition comprising the crystalline form of claim 6, and one or more pharmaceutically acceptable carriers or diluents.

23. A method of treating a disease or a disorder in a patient in need thereof, comprising administering to the patient a therapeutically effective amount of the crystalline form of claim 6, wherein the disease or disorder is selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

24. A pharmaceutical composition comprising the crystalline form of claim 7, and one or more pharmaceutically acceptable carriers or diluents.

25. A method of treating a disease or a disorder in a patient in need thereof, comprising administering to the patient a therapeutically effective amount of the crystalline form of claim 7, wherein the disease or disorder is selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, renal ischemia, rheumatoid arthritis, skeletal muscle contusion, skin diseases, sunburn, systemic lupus erythematosus, toothache, vasoocclusive painful crises in sickle cell disease, and visceral pain.

* * * * *

UNITED STATES PATENT AND TRADEMARK OFFICE
CERTIFICATE OF CORRECTION

PATENT NO. : 12,152,029 B2
APPLICATION NO. : 18/051654
DATED : November 26, 2024
INVENTOR(S) : Thomas Vetter et al.

It is certified that error appears in the above-identified patent and that said Letters Patent is hereby corrected as shown below:

In the Claims

Column 29, Lines 56 to 57, Claim 8, replace the text:
"to above 150-180° C. at a minimum of 2 minutes."
With:
-- to 150-180° C. at a minimum of 2 minutes. --

Signed and Sealed this
Twenty-seventh Day of May, 2025

Coke Morgan Stewart
*Acting Director of the United States Patent and Trademark Office*